(12) United States Patent
Drew et al.

(10) Patent No.: US 7,610,083 B2
(45) Date of Patent: Oct. 27, 2009

(54) METHOD AND SYSTEM FOR LOOP RECORDING WITH OVERLAPPING EVENTS

(75) Inventors: Touby A. Drew, Minneapolis, MN (US); David L. Carlson, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 350 days.

(21) Appl. No.: 11/380,575

(22) Filed: Apr. 27, 2006

(65) Prior Publication Data

US 2007/0255155 A1    Nov. 1, 2007

(51) Int. Cl.
*A61B 5/04*    (2006.01)
(52) U.S. Cl. .................................... 600/509
(58) Field of Classification Search ............ 600/509, 600/515, 521, 483, 544
See application file for complete search history.

(56) References Cited

U.S. PATENT DOCUMENTS

| | | | |
|---|---|---|---|
| 3,958,563 A | 5/1976 | Fernandez | |
| 4,374,382 A | 2/1983 | Markowitz | |
| 4,485,813 A | 12/1984 | Anderson | |
| 4,556,063 A | 12/1985 | Thompson | |
| 4,567,892 A | 2/1986 | Plicchi | |
| 4,583,553 A | 4/1986 | Shah | |
| 4,596,251 A | 6/1986 | Plicchi | |
| 4,903,701 A | 2/1990 | Moore | |
| 5,000,189 A * | 3/1991 | Throne et al. ............... 600/515 |
| 5,007,431 A | 4/1991 | Donehoo, III | |
| 5,052,388 A | 10/1991 | Sivula | |
| 5,127,404 A | 7/1992 | Wyborny | |
| 5,168,759 A | 12/1992 | Bowman | |
| 5,222,503 A * | 6/1993 | Ives et al. ................... 600/544 |
| 5,285,792 A | 2/1994 | Sjoquist | |
| 5,312,446 A | 5/1994 | Holschbach | |
| 5,336,244 A | 8/1994 | Weijand | |
| 5,354,318 A | 10/1994 | Taepke | |
| 5,409,009 A | 4/1995 | Olsen | |
| 5,518,001 A | 5/1996 | Snell | |
| 5,554,177 A | 9/1996 | Kieval | |
| 5,752,976 A | 5/1998 | Duffin | |
| 5,782,891 A | 7/1998 | Hassler | |
| 5,944,745 A | 8/1999 | Rueter | |
| 5,987,352 A | 11/1999 | Klein | |
| 5,995,868 A | 11/1999 | Dorfmeister | |
| 6,016,449 A | 1/2000 | Eischell | |
| 6,067,473 A | 5/2000 | Greeninger | |
| 6,128,538 A | 10/2000 | Fischell | |
| 6,200,265 B1 | 3/2001 | Walsh | |

(Continued)

FOREIGN PATENT DOCUMENTS

WO    2004/023983    3/2004

OTHER PUBLICATIONS

International Search Report, pp. 1-13, Aug. 29, 2007.

(Continued)

*Primary Examiner*—George Manuel
(74) *Attorney, Agent, or Firm*—John W. Albrecht

(57) ABSTRACT

A method and apparatus is provided for handling multiple loop recordings that result from events in a limited memory implantable device. The events may include various automatic and manual triggers. The method provides a mechanism for deciding the amount of information to store associated with each overlapping loop recording.

13 Claims, 15 Drawing Sheets

U.S. PATENT DOCUMENTS

| | | |
|---|---|---|
| 6,227,203 B1 | 5/2001 | Rise |
| 6,360,122 B1 | 3/2002 | Fischell |
| 6,427,086 B1 | 7/2002 | Fischell |
| 6,496,715 B1 | 12/2002 | Lee |
| 6,505,067 B1 | 1/2003 | Lee |
| 6,512,940 B1 | 1/2003 | Brabec |
| 6,522,915 B1 | 2/2003 | Ceballos |
| 6,549,804 B1 | 4/2003 | Osorio |
| 6,599,242 B1 | 7/2003 | Splett et al. |
| 6,664,729 B2 | 12/2003 | Elledge |
| 6,944,495 B2 * | 9/2005 | MacAdam et al. .......... 600/521 |
| 2004/0138536 A1 | 7/2004 | Frei |
| 2005/0081847 A1 | 4/2005 | Lee |
| 2005/0203366 A1 | 9/2005 | Donoghue |
| 2006/0224067 A1 * | 10/2006 | Giftakis et al. .............. 600/483 |

OTHER PUBLICATIONS

International Preliminary Report and Written Opinion for PCT/US2007/006365 mailed Nov. 6, 2008.

* cited by examiner

METHOD AND SYSTEM FOR LOOP RECORDING WITH OVERLAPPING EVENTS

FIELD OF THE INVENTION

The invention relates to techniques for selecting, storing and reporting data associated with physiologic signals that may be further associated with a neurological event.

BACKGROUND

Nervous system disorders affect millions of people, causing death and a degradation of life. Nervous system disorders include disorders of the central nervous system, peripheral nervous system, and mental health and psychiatric disorders. Such disorders include, for example without limitation, epilepsy, Parkinson's disease, essential tremor, dystonia, headache, and multiple sclerosis (MS). Additionally, mental health disorders and psychiatric disorders also include, but are not limited to, anxiety (such as general anxiety disorder, panic disorder, phobias, post traumatic stress disorder (PTSD), and obsessive compulsive disorder (OCD)), mood disorders (such as major depression, bipolar depression, and dysthymic disorder), sleep disorders (narcolepsy), obesity, and anorexia.

As an example, epilepsy is a prevalent serious neurological disease across all ages. Epilepsy is a group of neurological conditions in which a person has or is predisposed to recurrent seizures. A seizure is a clinical manifestation resulting from excessive, hypersynchronous, abnormal electrical or neuronal activity in the brain. (A neurological event is an activity that is indicative of a nervous system disorder. A seizure is a type of a neurological event.) This electrical excitability of the brain may be likened to an intermittent electrical overload that manifests with sudden, recurrent, and transient changes of mental function, sensations, perceptions, and/or involuntary body movement. Because seizures can be unpredictable, epilepsy affects a person's employability, psychosocial life, and ability to operate vehicles or power equipment. It is a disorder that occurs in all age groups, socioeconomic classes, cultures, and countries. In developed countries, the age-adjusted incidence of recurrent unprovoked seizures ranges from 24/100,000 to 53/100,000 person-years and may be even higher in developing countries. In developed countries, age specific incidence is highest during the first few months of life and again after age 70. The age-adjusted prevalence of epilepsy is 5 to 8 per 1,000 (0.5% to 0.8%) in countries where statistics are available. In the United States alone, epilepsy and seizures affect 2.3 million Americans, with approximately 181,000 new cases occurring each year. It is estimated that 10% of Americans will experience a seizure in their lifetimes, and 3% will develop epilepsy by age 75.

There are various approaches in treating nervous system disorders. Treatment therapies can include any number of possible modalities alone or in combination including, for example, electrical stimulation, magnetic stimulation, drug infusion, and/or brain temperature control. Each of these treatment modalities can be operated using closed-loop feedback control. Such closed-loop feedback control techniques receive from a monitoring element a neurological signal that carries information about a symptom or a condition or a nervous system disorder. Such a neurological signal can include, for example, electrical signals (such as EEG, ECoG, and/or EKG), chemical signals, other biological signals (such as change in quantity of neurotransmitters), temperature signals, pressure signals (such as blood pressure, intracranial pressure or cardiac pressure), respiration signals, heart rate signals, pH-level signals, and nerve signals (such as cuff electrodes on a peripheral nerve). Monitoring elements can include, for example, recording electrodes or various types of sensors.

For example, U.S. Pat. No. 5,995,868 discloses a system for the prediction, rapid detection, warning, prevention, or control of changes in activity states in the brain of a patient. Use of such a closed-loop feed back system for treatment of a nervous system disorder may provide significant advantages in that treatment can be delivered before the onset of the symptoms of the nervous system disorder.

During the operation of a medical device system, the patient is likely to experience multiple detections of the nervous system disorder. For example, in the case of seizures, the patient may have thousands of seizures over the course of a time period, but only a few of those may have behavioral manifestations. The other seizure episodes that don't exhibit behavioral manifestations are considered sub-clinical or electrographic seizures. When the medical device system monitors for seizure occurrences, however, the medical device system may detect many seizure events although only some of these events will spread to other parts of the brain such that the patient will exhibit it (e.g., convulsions, unconsciousness, etc.).

In order to effectively provide treatment therapy, an implanted device may be required to record physiologic data that is related to the disorder. However, an implanted device is typically limited by memory capacity and by battery capacity. Thus, the implanted device is limited in the amount of data that can be stored and reported.

An implanted device may store physiologic data in a data structure and manage memory allocation for the data structure. However, the memory allocation management supported by the implanted device may have deficiencies. For example, with a FIFO memory buffer if the amount of collected physiologic data exceeds the available memory space, the oldest physiologic data is lost regardless of the importance of the lost data.

It is therefore desirable to selectively store physiologic data in the limited memory space of an implanted device. The implanted device can report the most relevant data from the stored data so that the implanted device can be configured to provide efficacious treatment.

SUMMARY

The following represents a simplified summary of some embodiments of the invention in order to provide a basic understanding of various aspects of the invention. This summary is not an extensive overview of the invention nor is it intended to identify key or critical elements of the invention or to delineate the scope of the invention. Its sole purpose is to present aspects of the invention in simplified form as a prelude to the more detailed description that is presented thereafter.

In accordance with an aspect of the invention, an implantable medical device stores loop recordings of waveform data having specified pre-event and post-event times. The implantable medical device includes multiple sense channels to process numerous signal types. In an embodiment of the invention, various types of triggers may cause the implantable medical device to store waveform data. The triggers may include an implantable seizure detection algorithm which monitors EEG channels for seizure activity. In addition, the triggers may include cardiac arrhythmia detection logic to monitor ECG signals. Moreover, the triggers may include manual triggers operated by a patient through a patient programmer.

In accordance with another aspect of the invention, a method and apparatus is provided for handling multiple loop recording triggers and their associated overlaps in a limited memory device. The method provides a mechanism for deciding what and how much information to store for events.

In a further aspect of the invention, a first event associated with brain activity may be detected. Based on the detection a first loop recording may be initiated. The first loop recording may include a pre-event time and post-event time. In addition, a second event associated with heart activity may also be detected. A determination may be made whether to initiate a second loop recording for the second event based on loop overlap and the status of the post-event recording associated with the first loop recording.

DETAILED DESCRIPTION OF THE INVENTION

Figure 1:
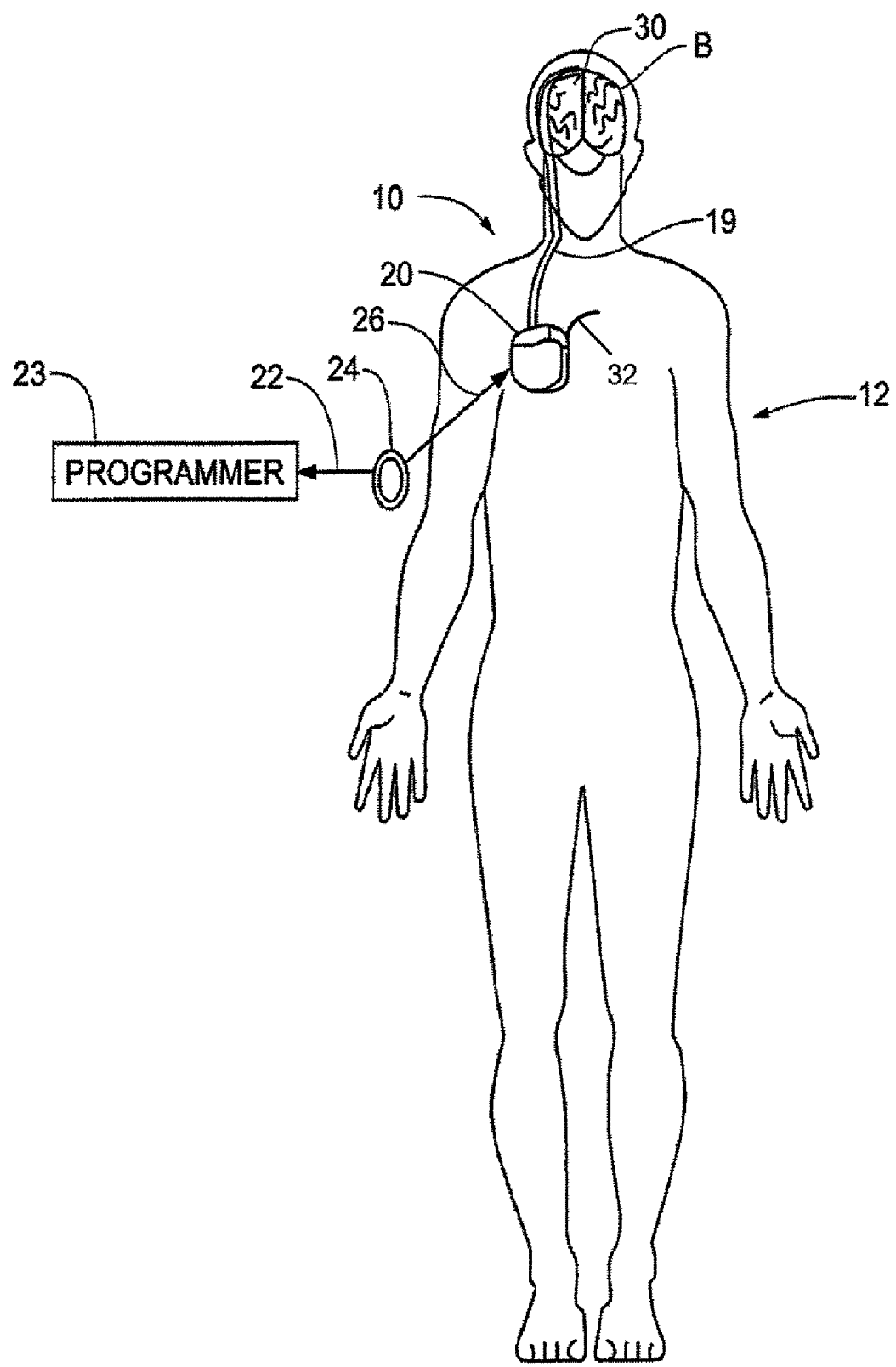
FIG. 1 is a schematic view of a medical device implanted in a patient that monitors cardiac and nervous system disorders in accordance with an aspect of the invention.

The following description discloses techniques for selecting, storing and reporting data associated with physiologic signals that may be further associated with a neurological event. These techniques are suitable for use within any implantable medical device system. For example, an implantable medical device may consist of ECG and EEG inputs. The monitoring device may monitor the neural or cardiac inputs in various combinations.

In an embodiment, the invention may be implemented within an implantable neurostimulator system, however, as already discussed, those skilled in the art will appreciate that the techniques disclosed herein may be implemented generally within any implantable medical device system having monitoring capabilities of physiological conditions of the patient including, but not limited to, implantable drug delivery systems, implantable systems providing stimulation and drug delivery, pacemaker systems, defibrillator systems, cochlear implant systems, and implantable diagnostic system for detecting bodily conditions, including those in organs like the brain and/or the heart. The implantable medical device may provide therapeutic treatment to neural tissue in any number of locations in the body including, for example, the brain (which includes the brain stem), the vagus nerve, the spinal cord, peripheral nerves, etc. The treatment therapies can include any number of possible modalities alone or in combination including, for example, electrical stimulation, magnetic stimulation, drug infusion, brain temperature control, and/or any combination thereof.

In addition, aspects of the invention may be embodied in various forms to analyze and treat nervous system and other disorders, namely disorders of the central nervous system, peripheral nervous system, and mental health and psychiatric disorders. Such disorders include, for example without limitation, epilepsy, Sudden Unexpected Death in Epilepsy Patients (SUDEP), Parkinson's disease, essential tremor, dystonia, multiple sclerosis (MS), anxiety (such as general anxiety, panic, phobias, post traumatic stress disorder (PTSD), and obsessive compulsive disorder (OCD)), mood disorders (such as major depression, bipolar depression, and dysthymic disorder), sleep disorders (narcolepsy), obesity, tinnitus, stroke, traumatic brain injury, Alzheimer's, and anorexia.

The physiologic signals that are selected, stored and reported in accordance with various aspects of the invention may include any number of sensed signals. Such physiological signals can include, for example, electrical signals (such as EEG, ECoG and/or EKG), chemical signals, biological signals (such as change in quantity of neurotransmitters), temperature signals, pressure signals (such as blood pressure, intracranial pressure or cardiac pressure), respiration signals, heart rate signals, pH-level signals, activity signals (e.g., detected by an accelerometer), and/or peripheral nerve signals (cuff electrodes on a peripheral nerve). Such physiological signals may be recorded using one or more monitoring elements such as monitoring electrodes or sensors. For example, U.S. Pat. No. 6,227,203 provides examples of various types of sensors that may be used to detect a symptom or a condition or a nervous system disorder and responsively generate a neurological signal. In addition, various types of physiologic activities may be sensing including, for example, brain, heart and/or respiration.

As discussed, the techniques disclosed herein are suitable for use within any implantable medical device system that receives signals associated with the physiological conditions being sensed, a memory component, and a processing component (logic or software) that stores data records in data structures.

In an aspect of the invention, the medical device monitors cardiac (ECG) and neural (EEG) signals and records these signals as discussed herein. Real-time analysis of the ECG signal evaluates rate disturbances (e.g., bradycardia; tachycardia; asystole) as well as any indications of cardiac ischemia (e.g., ST segment changes; T wave inversion, etc). Abnormalities detected during real-time analysis may lead to an immediate patient alert, which can be audible (beeps, buzzers, tones, spoken voice, etc.), light, tactile, or other means. Manual indication of a seizure or other event may be achieved through an external programmer device. The patient (or caregiver) may push a button on the external programmer device, while communicating with the implanted device. This will provide a marker and will initiate a recording, as discussed herein, of the sensed data (for example, in the event the patient is experiencing a neurological event).

In assessing the risk of SUDEP, for example, prolonged ECG recordings may be possible (e.g., recording all data during sleep since the incidence of SUDEP is highest in patients during sleep). Post-processing of the signal can occur in the implanted device, the patient's external device, a clinician external device, and/or another computing device. Intermittently (e.g., every morning, once/week, following a seizure), a patient may download data from the implantable device to the patient external device (as will be discussed further herein), which may then be analyzed by the external device (and/or sent through a network to the physician) to assess any ECG abnormalities. If an abnormality is detected, the device may notify the patient/caregiver. At that time, the patient/caregiver may inform the healthcare provider of the alert to allow a full assessment of the abnormality. The clinician external device may also be capable of obtaining the data from the implanted device and conducting an analysis of the stored signals. If a potentially life-threatening abnormality is detected, the appropriate medical treatment may be prescribed (e.g., cardiac abnormality: a pacemaker, an implantable defibrillator, or a heart resynchronization device may be indicated or respiration abnormality: CPAP, patient positioning, or stimulation of respiration may be indicated).

Moreover, the implantable medical device may also monitor EEG signals from intracranially implanted leads. This may allow the implanted medical device to collect cardiovascular and neurological signals in close proximity to detected neurological events as well as notify the patient/caregiver of a prolonged event (and/or status epilepticus). The implantable medical device may detect neurological events and analyze the peri-ictal signals and initiate loop recording.

Again, it will be appreciated that alternative embodiments of the implantable medical device may also be utilized. For example, cardiac lead(s), a sensor stub, and/or a wearable patch may be used to facilitate detection of a neurological event and the recording of data and signals pre and post event. An integrated electrode may also be used that senses ECG signals as described in U.S. Pat. No. 5,987,352. Optionally, the implantable medical device may warn/alert the patient 12 via buzzes, tones, beeps or spoken voice (as substantially described in U.S. Pat. No. 6,067,473) via a piezo-electric transducer incorporated into the housing of implantable medical device. The sound may be transmitted to the patient's inner ear.

In another embodiment, the monitor may be implanted cranially in the patient 12 (FIG. 1). In such an embodiment, the monitor may be constructed as substantially described in U.S. Pat. Nos. 5,782,891 and 6,427,086. EEG sensing may be accomplished by the use of integrated electrodes in the housing of the monitor, cranially implanted leads, and or leadless EEG sensing.

FIG. 1 illustrates an implantable system 10 including an implantable medical device 100 implanted in a patient 12. The implantable medical device 100 continuously senses and monitors one or more physiological conditions of the patient via lead 19 and monitoring/sensing elements 30 and 32 (in the embodiment, the physiological conditions are cardiac and neurological functions of patient 12). Stored diagnostic data is uplinked and evaluated by an external computing device 23 (e.g., a patient's or physician's programmer) via a 2-way telemetry, using for example, antenna 24 to relay radio frequency signals 22, 26 between implantable medical device 100 and external computing device 23. An external patient activator that may be located on external computing device 23 may optionally allow patient 12, or care provider (not shown), to manually activate the recording of diagnostic data.

Figure 2:
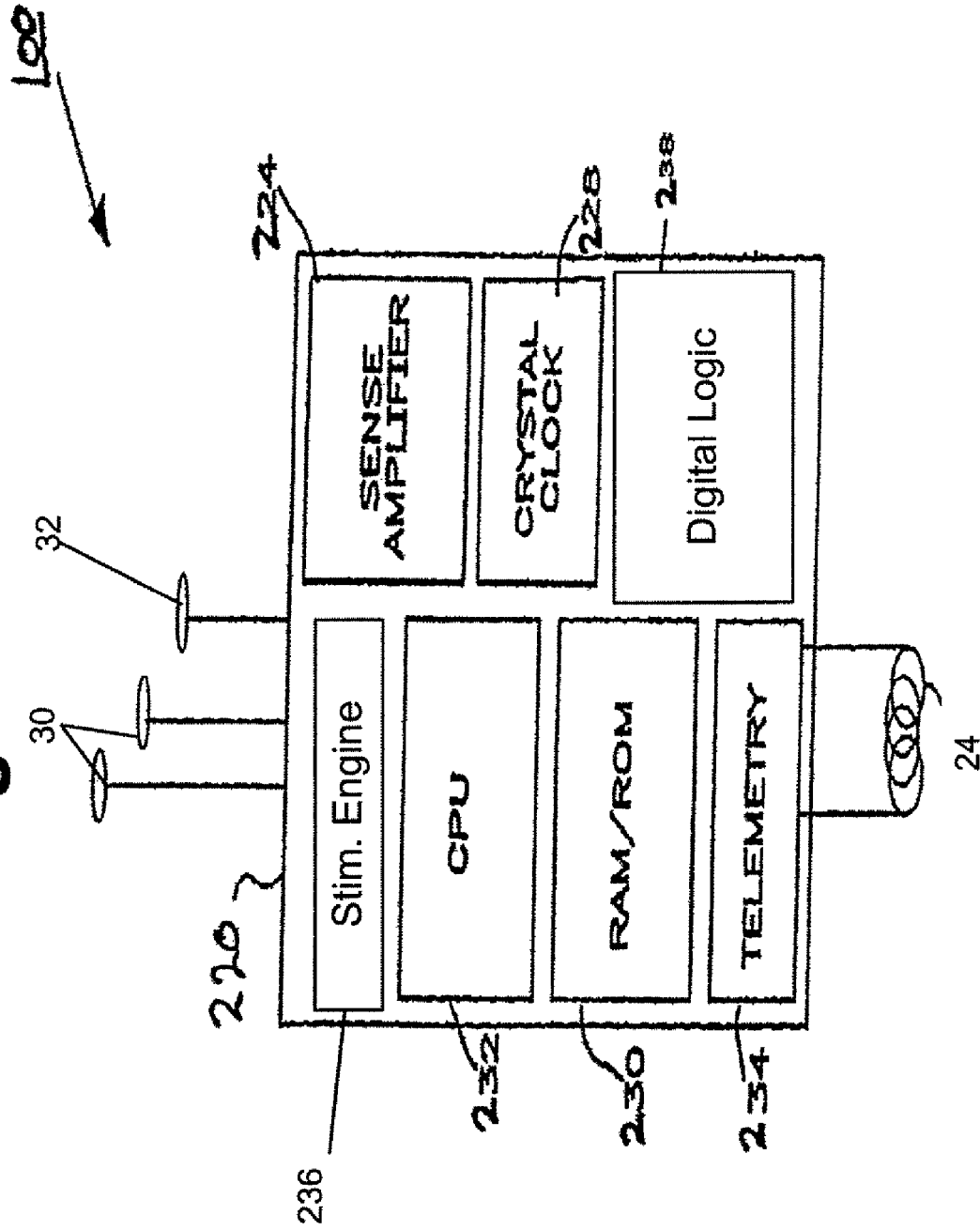
FIG. 2 is a simplified block diagram of the medical device shown in FIG. 1 in accordance with an aspect of the invention.

FIG. 2 depicts a block diagram of the electronic circuitry of implantable medical device 100 of FIG. 1 in accordance with an embodiment of the invention. Implantable medical device 100 comprises a primary control circuit 220 and may be similar in design to that disclosed in U.S. Pat. No. 5,052,388. Primary control circuit 220 includes sense amplifier circuitry 224, a crystal clock 228, a random-access memory and read-only memory (RAM/ROM) unit 230, a central processing unit (CPU) 232, digital logic circuit 238, a telemetry circuit 234, and stimulation engine circuitry 236, all of which are generally known in the art.

Implantable medical device 100 may include internal telemetry circuit 234 so that it is capable of being programmed by means of external programmer/control unit 23 via a 2-way telemetry link. External programmer/control unit 23 communicates via telemetry with implantable medical device 100 so that the programmer can transmit control commands and operational parameter values to be received by the implanted device, and so that the implanted device can communicate diagnostic and operational data to the programmer 23. For example, programmer 23 may be Models 9790 and CareLink® programmers, commercially available from Medtronic, Inc., Minneapolis, Minn. Various telemetry systems for providing the necessary communications channels between an external programming unit and an implanted device have been developed and are well known in the art. Suitable telemetry systems are disclosed, for example, in U.S. Pat. Nos. 5,127,404; 4,374,382; and 4,556,063.

Typically, telemetry systems such as those described in the above referenced patents are employed in conjunction with an external programming/processing unit. Most commonly, telemetry systems for implantable medical devices employ a radio-frequency (RF) transmitter and receiver in the device, and a corresponding RF transmitter and receiver in the external programming unit. Within the implantable device, the transmitter and receiver utilize a wire coil as an antenna 24 for receiving downlink telemetry signals and for radiating RF signals for uplink telemetry. The system is modeled as an air-core coupled transformer. An example of such a telemetry system is shown in U.S. Pat. No. 4,556,063.

In order to communicate digital data using RF telemetry, a digital encoding scheme such as is described in U.S. Pat. No. 5,127,404 can be used. In particular, a pulse interval modulation scheme may be employed for downlink telemetry, wherein the external programmer transmits a series of short RF "bursts" or pulses in which the interval between successive pulses (e.g., the interval from the trailing edge of one pulse to the trailing edge of the next) is modulated according to the data to be transmitted. For example, a shorter interval may encode a digital "0" bit while a longer interval encodes a digital "1" bit. For uplink telemetry, a pulse position modulation scheme may be employed to encode uplink telemetry data. For pulse position modulation, a plurality of time slots are defined in a data frame, and the presence or absence of pulses transmitted during each time slot encodes the data. For example, a sixteen-position data frame may be defined, wherein a pulse in one of the time slots represents a unique four-bit portion of data.

Programming units such as the above-referenced Medtronic Models 9790 and CareLink® programmers typically interface with the implanted device through the use of a programming head or programming paddle, a handheld unit adapted to be placed on the patient's body over the implant site of the patient's implanted device. A magnet in the programming head effects reed switch closure in the implanted device to initiate a telemetry session. Thereafter, uplink and downlink communication takes place between the implanted device's transmitter and receiver and a receiver and transmitter disposed within the programming head.

As previously noted, primary control circuit 220 includes central processing unit 232 which may be an off-the-shelf programmable microprocessor or microcontroller, but in an embodiment of the invention it may be a custom integrated circuit. Although specific connections between CPU 232 and other components of primary control circuit 220 are not shown in FIG. 2, it will be apparent to those of ordinary skill in the art that CPU 232 functions to control the timed operation of sense amplifier circuit 224 under control of programming stored in RAM/ROM unit 230. In addition to or as an alternative embodiment digital logic 238 may also be provided and utilized. In another alternative embodiment, a processing module that contains either a processor or digital circuitry may also be utilized. Those of ordinary skill in the art will be familiar with such an operative arrangement.

With continued reference to FIG. 2, crystal oscillator circuit 228 provides main timing clock signals to primary control circuit 220. The various components of implantable medical device 100 are powered by means of a battery (not shown), which is contained within the hermetic enclosure of implantable medical device 100. For the sake of clarity in the figures, the battery and the connections between it and the other components of implantable medical device 100 are not shown. Sense amplifier 224 is coupled to monitoring/sensing elements 30 and 32. Where cardiac intrinsic signals are sensed, they may sensed by sense amplifier 224 as substantially described in U.S. Pat. No. 6,505,067.

Processing by CPU 232 or digital logic 238 allows detection of cardiac and neural electrical characteristics and anomalies. Upon detection of either a cardiac or neural anomaly, CPU 232 or digital logic 238, under control of firmware resident in RAM/ROM 230, will initiate recording of the appropriate diagnostic information into RAM of RAM/ROM 230 (discussed further herein), an may initiate a warning or alert to the patient, patient caregiver, or remote monitoring location.

Figure 3:
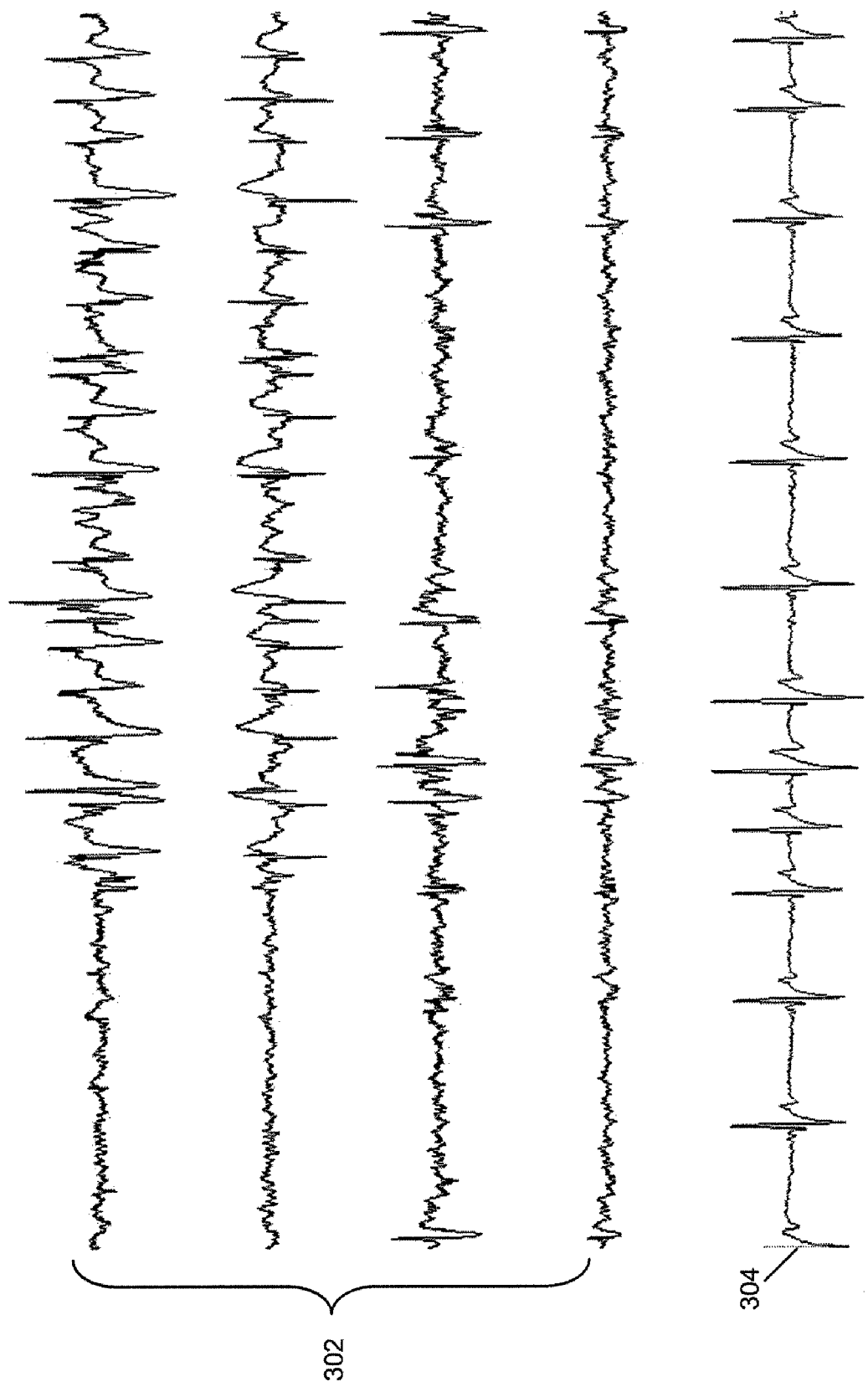
FIG. 3 is a graphical representation of various signals sensed by the medical device as shown in FIG. 1 in accordance with an aspect of the invention.

The recording of EEG and ECG signal simultaneously may allow a physician to assess the interplay between brain and cardiac signals, particularly when a seizure and/or cardiac arrhythmia are present. For example, FIG. 3 shows the interplay between EEG signals 302 and ECG signal 304. Both EEG signals 302 and the ECG signal 304 may be presented to sense amplifier 224 from monitoring elements 30 and 32. Note the amplitude variation of cardiac signals may be caused by the change in thoracic cavity pressure due to respiration (i.e., inspiration and expiration).

It will be appreciated that alternative embodiments of implantable medical device 100 may also be utilized. As discussed above, implantable medical device 100 may sense any number of physiologic conditions of the patient 12 for purposes of detecting, and storing data relating to, any number of the neurological events. For example, various lead(s) may be used to facilitate detection of a neurological event and the recording of data and signals pre and post event. For example, cardiac leads may consist of any typical lead configuration as is known in the art, such as, without limitation, right ventricular (RV) pacing or defibrillation leads, right atrial (RA) pacing or defibrillation leads, single pass RA/RV pacing or defibrillation leads, coronary sinus (CS) pacing or defibrillation leads, left ventricular pacing or defibrillation leads, pacing or defibrillation epicardial leads, subcutaneous defibrillation leads, unipolar or bipolar lead configurations, or any combinations of the above lead systems.

In another aspect of the invention, an electrode 32 located distally on a sensor stub may be used to facilitate detection of a neurological event and the recording of data and signals pre and post event. The sensor stub 32 is inserted subcutaneously in a thoracic area of the patient 12. The implantable medical device 100 may sense cardiac signals between an electrode on the distal end of the sensor stub and the implantable medical device case as described in conjunction with the embodiment shown in FIG. 5 in U.S. Pat. No. 5,987,352. In alternative embodiments of the invention, the implantable medical device 100 may also sense respiration parameters such as respiration rate, minute ventilation and apnea via measuring and analyzing the impedance variations measured from the implanted implantable medical device 100 case to the electrode located distally on the sensor stub lead as substantially described in U.S. Pat. Nos. 4,567,892 and 4,596,251.

In yet another aspect of the invention, an external wearable device such as a wearable patch, a wristwatch, or a wearable computing device may be used may be used to continuously sense and implantable medical device cardiac functions of patient 12. Optionally, a button (not shown) on the external wearable device may be activated by the patient 12 (or a caregiver) to manually activate data recording (for example, in the event the patient is experiencing a neurological event). The external wearable device may comprise an amplifier, memory, microprocessor, receiver, transmitter and other electronic components as substantially described in U.S. Pat. No. 6,200,265. In the embodiment of a wearable patch, the device may consist of a resilient substrate affixed to the patient's skin with the use of an adhesive. The substrate flexes in a complimentary manner in response to a patient's body movements providing patient comfort and wearability. The low profile patch is preferably similar in size and shape to a standard bandage, and may be attached to the patient's skin in an inconspicuous location.

As exemplified above, any number of implantable medical device systems are envisioned that may incorporate the recording and retention techniques discussed herein. For example, the monitoring may be achieved using any of the above techniques in conjunction with treatment by delivery of treatment therapy (e.g., electrical stimulation) to the brain, cardiac or respiration.

The above embodiments illustrate that the disclosed techniques may be implemented within any number of medical device systems (drug delivery, electrical stimulation, pacemaking, defibrillating, cochlear implant, and/or diagnostic) but configured to retain sensed data records in accordance with the teachings disclosed herein. In general, the implanted medical component utilizes one or more monitoring elements (e.g., electrodes or other sensors), a memory component having a plurality of data structures (and/or data structure types), a processing component (such as a CPU or digital logic) to process received data for storage in memory as disclosed herein, and a telemetry component.

Figure 4:
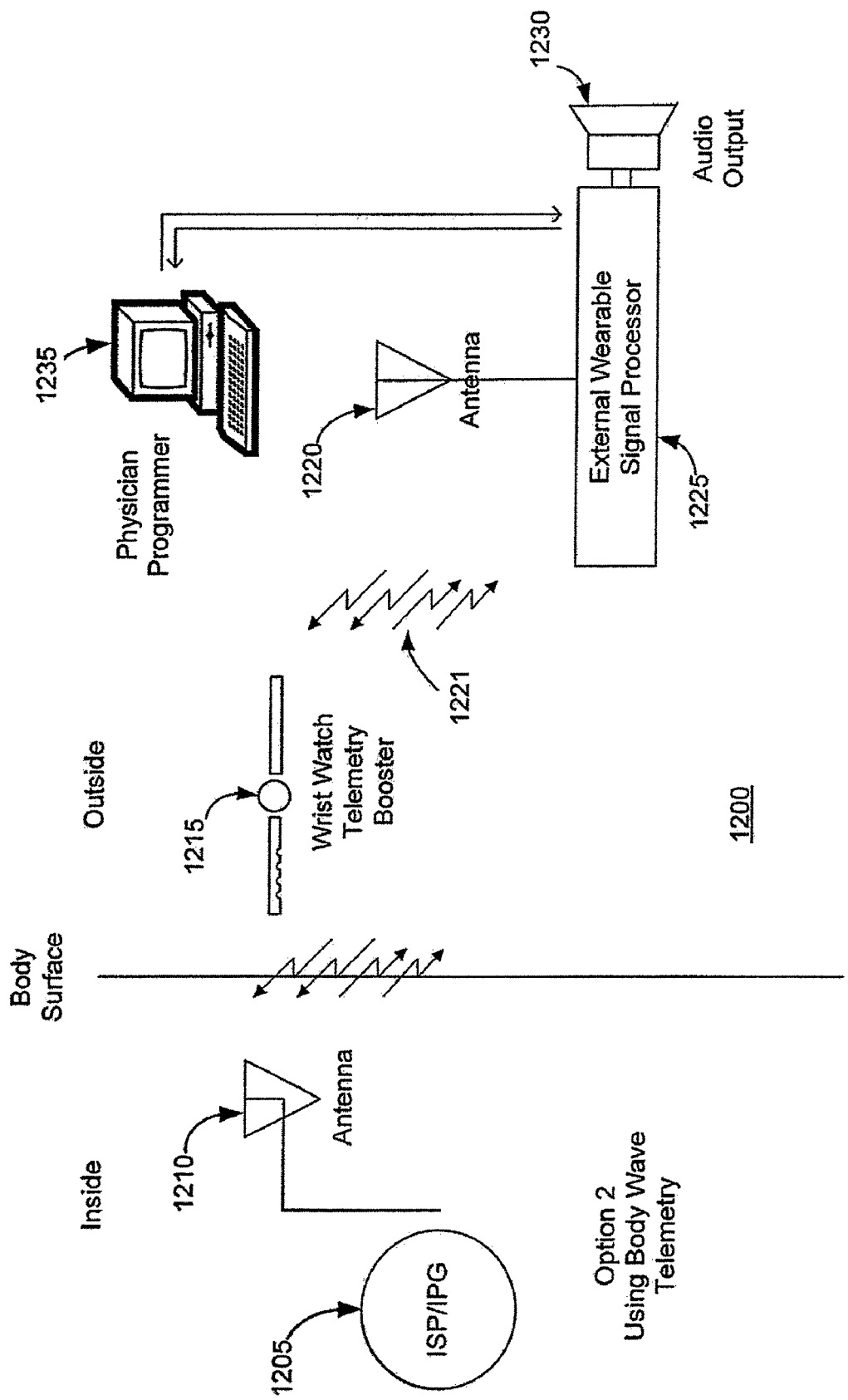
FIG. 4 shows an apparatus that supports reporting neurological data in accordance with an aspect of the invention.

FIG. 4 shows apparatus 1200 that supports reporting physiological data in accordance with an aspect of the invention. With apparatus 1200, the implanted component 1205 of the medical device system communicates with the relaying module 1215 via telemetry antenna 1210. Similarly, the external component 1225 communicates with the relaying module 1215 via antenna 1220. In the embodiment, a telemetry link 1221 between relaying module 1215 and antenna 1220 comprises a 3 MHz body wave telemetry link. To avoid interference, the relaying module 1215 may communicate with the external and implanted components using differing communication schemes. In some embodiments, the reverse direction and the forward direction of telemetry link 1221 may be associated with different frequency spectra. The relaying module 1215 thereby provides a greater range of communications between components of medical device system. For example, in the embodiment of an implanted system, an external programmer may communicate with an implanted device from a more remote location. The external programmer may be across the room and still be in communication via the relaying module 1215. With the telemetry booster stage, the use of an implanted system is more convenient to the patient, in particular at night while sleeping or when taking a shower, eliminating the need for an external device to be worn on the body.

Figure 5:
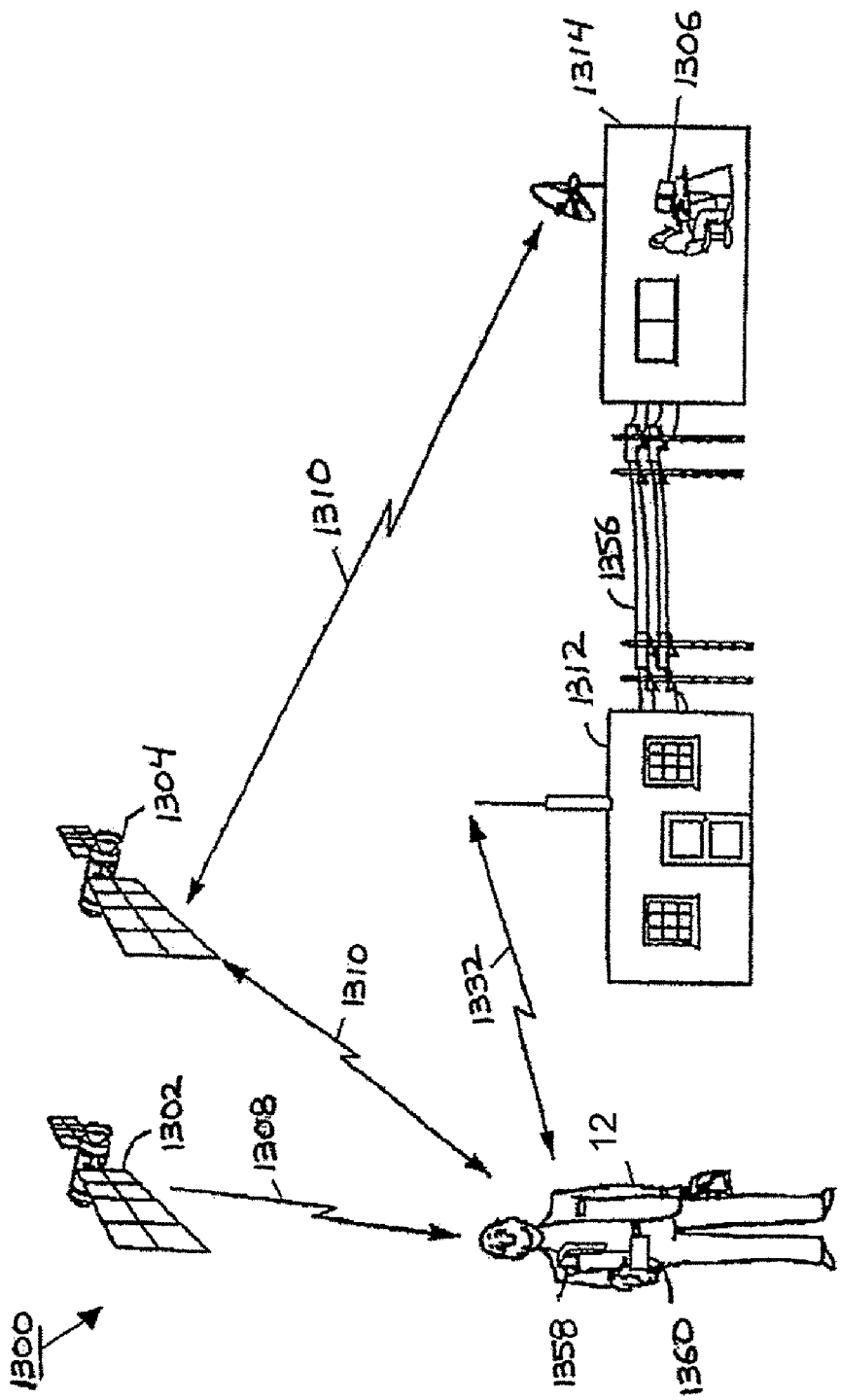
FIG. 5 is a schematic diagram of a system utilizing the above-described embodiments and allowing remote monitoring and diagnostic evaluation of at risk patients in accordance with an aspect of the invention.

As shown in FIG. 5, in an embodiment, the system allows the residential, hospital or ambulatory monitoring of at-risk patients and their implanted medical devices at any time and anywhere in the world. Medical support staff 1306 at a remote medical support center 1314 may interrogate and read telemetry from the implanted medical device and reprogram its operation while the patient 12 is at very remote or even unknown locations anywhere in the world. Two-way voice communications 1310 via satellite 1304, via cellular link 1332 or land lines 1356 with the patient 12 and data/programming communications with the implanted medical device 1358 via a belt worn transponder 1360 may be initiated by the patient 12 or the medical support staff 1306. The location of the patient 12 and the implanted medical device 1358 may be determined via GPS 1302 and link 1308 and communicated to the medical support network in an emergency. Emergency response teams can be dispatched to the determined patient location with the necessary information to prepare for treatment and provide support after arrival on the scene. See for example, U.S. Pat. No. 5,752,976.

Figure 6:
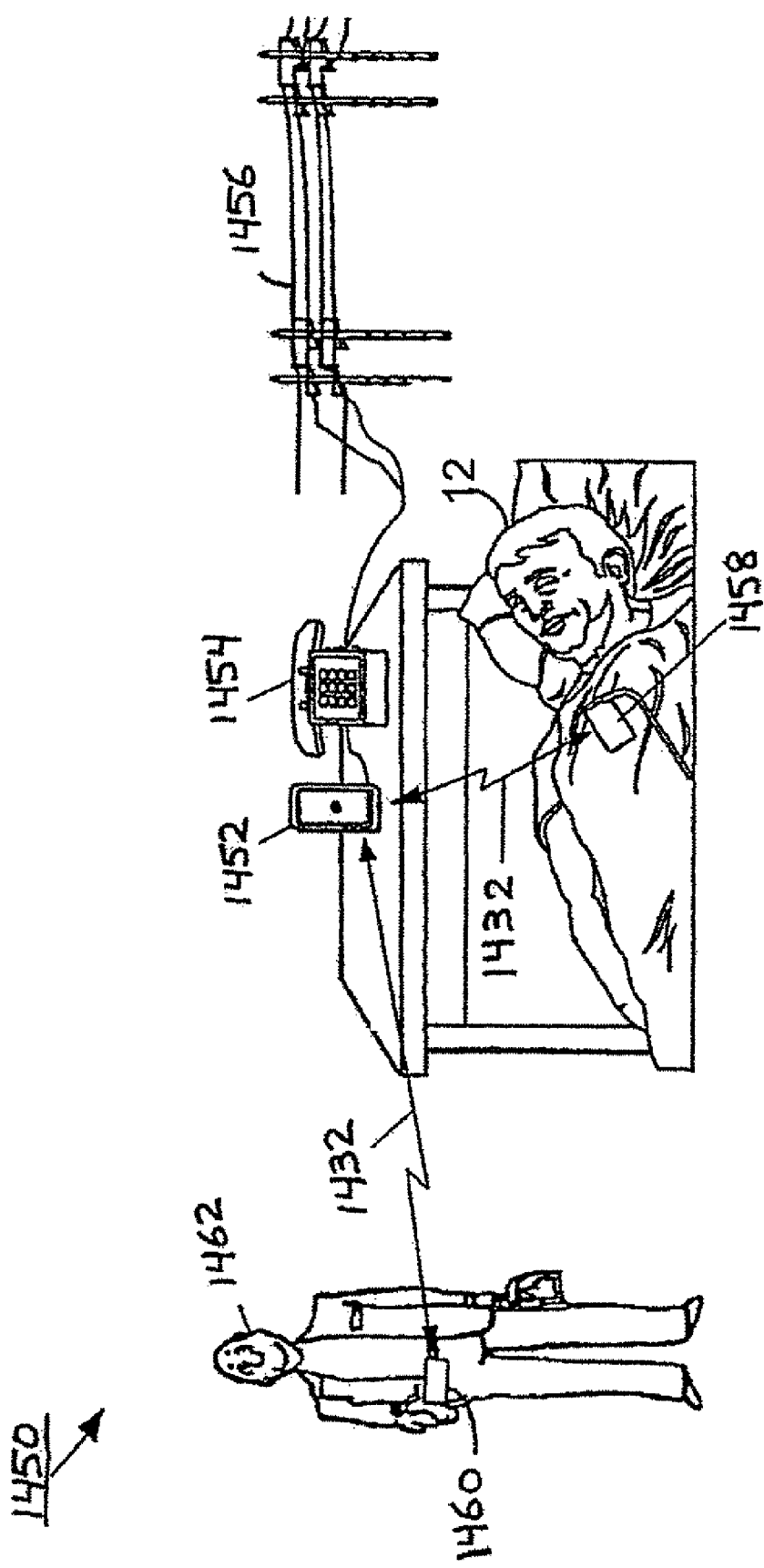
FIG. 6 is a schematic diagram of an alternative system utilizing the above-described embodiments and allowing remote monitoring and diagnostic evaluation of at risk patients in accordance with an aspect of the invention.

An alternative or addition to the remote monitoring system as described above in conjunction with FIG. 5 is shown in the system 1450 of FIG. 6, which shows a patient 12 sleeping with an implantable Monitor 1458 and/or optional therapy device as described above in connection with the above-described systems. The implantable device 1458, upon detection of a neurologic event may alert a remote monitoring location via local remote box 1452 (as described in U.S. Pat. No. 5,752,976), telephone 1454 and phone lines 1456 or the patient's care provider via an RF link 1432 to a pager-sized remote monitor 1460 placed in other locations in the house or carried (i.e., belt worn) by the care provider 1462. The remote caregiver monitor 1460 may include audible buzzes/tones/beeps, vocal, light and/or vibration to alert the caregiver 1462 of patient's monitor in an alarm/alert condition. The RF link may include RF portable phone frequencies, power line RF links, HomeRF, Bluetooth, ZigBee, WIFI, MICS band (medical implant communications service), or any other interconnect methods as appropriate.

In another aspect of the invention, techniques for selecting and storing sensed physiological data in an implanted medical device for subsequent reporting to an external device are disclosed. As used herein, the term data record encompasses the sensed physiological data, summary information, or simply a pointer that references a location in memory where the sensed physiological data is stored. Thus, the concept of storage of data records in first and second data structures envisions possibilities of storage of the sensed physiological data and the storage of their associated pointers. As an example, summary information data may be stored in the first and second data structures wherein the more detailed and more space consuming waveform data (pre-detection data, post-detection data, etc.) may be stored, and pointed to, in an associated memory (such as a loop record buffer).

Mapping from entries in the first and second data structures to the waveform physiological data that is stored in the associated memory may be achieved with pointers. Each entry in the event log may point to its corresponding waveform data, or each waveform data may point to its corresponding data in the event log. Alternatively, multi-directional pointers in an "allocation table" or "allocation data structure" may be pointed to by the priority structures. Thus, when a data record is overwritten or replaced as discussed herein, both the data record itself and its mapping to the event log may be changed/removed in the allocation structure.

In an embodiment, the implantable medical device may have a set of monitoring elements sensing brain activity and another set of monitoring element that sense a physiological activity other than the brain (e.g., heart activity such as a heart arrhythmia and/or respiratory activity). The device may then implement a detection algorithm to determine the possible onset of a possible neurological event (e.g., a seizure) based on the sensed signals from either the first or second monitoring elements. Once a neurological event is detected, data records associated with the first and second monitoring elements may be stored in memory in accordance with the teachings herein.

Alternatively or additionally, the device may initiate loop recording upon indication to do so by the patient based, for example, on a patient detecting a neurological event. In the event the patient initiates loop recording based on detection of a neurological event (wherein, however, the detection process of the implanted device has not detected the neurological event), the priority index (discussed below) for such data may be set at a higher level such that the data is stored in a memory. In the situation where the patient experiences a neurological event but the medical device has not detected the event, the physiological sensed data may be particularly important for storage and subsequent evaluation. In an exemplary embodiment, once activated by a patient, loop recording may save the data for 30 seconds before the indicated seizure and 3 minutes after the seizure. However, to allow for the fact that the patient may not mark the seizure until the seizure has ended, the ECG loop recording may begin 3 to 5 minutes before the patient mark. This time period may be programmable. In another aspect of the invention, the ECG loop recording may begin before the patient mark from a time period ranging between 30 seconds to one hour. As discussed below, a subset or a composite of physiologic channels is selected from the available physiologic channels based on a selection criterion.

In an aspect of the invention, a priority index may be utilized to organize different recorded events. The priority index may be expressed as a mathematical combination of the severity level function $f(x_1, x_2, \ldots, x_n)$ and the associated factor function $g(y_1, y_2, \ldots y_m)$. For example, the priority level may be expressed as:

$$\text{priority index} = f(x_1, x_2, \ldots, x_n) + g(y_1, y_2, \ldots y_m) \quad \text{(EQ. 1A)}$$

Either $f(x_1, x_2, \ldots, x_n)$ or $g(y_1, y_2, \ldots y_m)$ may be a continuous function, a discrete-value function, a Boolean function, or a combination of the above function types. As another example, the priority level may be expressed as:

$$\text{priority index} = f(x_1, x_2, \ldots, x_n) \cdot g(y_1, y_2, \ldots y_m) \quad \text{(EQ. 1B)}$$

The priority index may be more generally expressed as a function $h(z_1, z_2)$, where $$\text{priority index} = h(f(x_1, x_2, \ldots, x_n), g(y_1, y_2, \ldots y_m)) \quad \text{(EQ. 1C)}$$

In accordance with an aspect of the invention, in response to an instruction from a clinician, an implanted device organizes stored physiological data according to the associated priority index and reports a predetermined number of data records that are deemed as having a higher priority index than the other stored data records.

The above approach may be extended to include the retention of more than one channel from a channel list sorted by relevancy as determined by a function of various factors (e.g., onset time, presence and severity of an event) as previously discussed. One may keep the most relevant physiologic channels of the channel list. For example, one may keep the three most relevant ("interesting") physiologic channels of five physiologic channels. Keeping the two or most relevant physiologic channels is referred as the "multi-max" of the channel list.

With an embodiment of the invention, the selection of physiologic channels may occur after filtering (e.g., bandpass, notch, FIR, and IIR) the physiologic channels. For example, an EEG signal may be filtered in the 10-60 Hz range to remove the bulk of the EEG energy content that may otherwise mask the ictal content. As another example, the physiologic channels may be filtered in the 180-250 Hz range in order to study "fast-ripple" events.

In another aspect of the invention, techniques for storing recording of event data in an implanted medical device for subsequent reporting and analysis are disclosed. Due to memory constraints of implantable devices, the storage of duplicative overlapping data should be avoided. As those skilled in the art will realize, a computing device with an associated computer readable-medium containing instructions for controlling the computing device may be utilized to implement the exemplary embodiments that are disclosed in this description.

In an aspect of the invention, all events are logged into an event recorder regardless of whether data specific to a particular event is saved or overwritten due to full memory. Furthermore, in another aspect of the invention, all pre-event and post-event times may be the same for all events. However, as those skilled in the art will realize both pre-event and post-event times may be adjusted such that the total time saved for each event remains the same.

Figure 7:
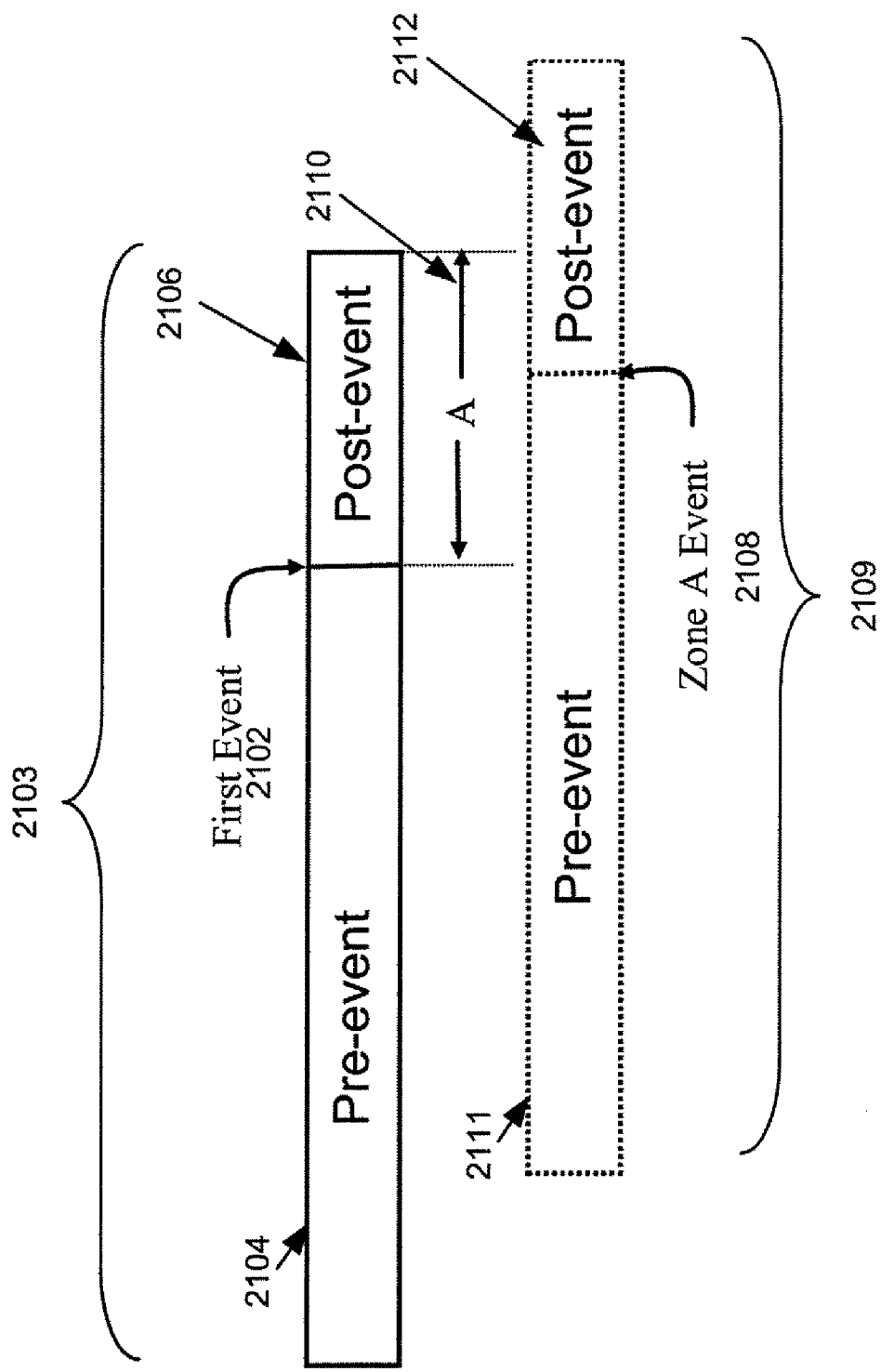
FIG. 7 shows a first scenario of an overlap of events recording in accordance with an aspect of the invention.
Figure 8:
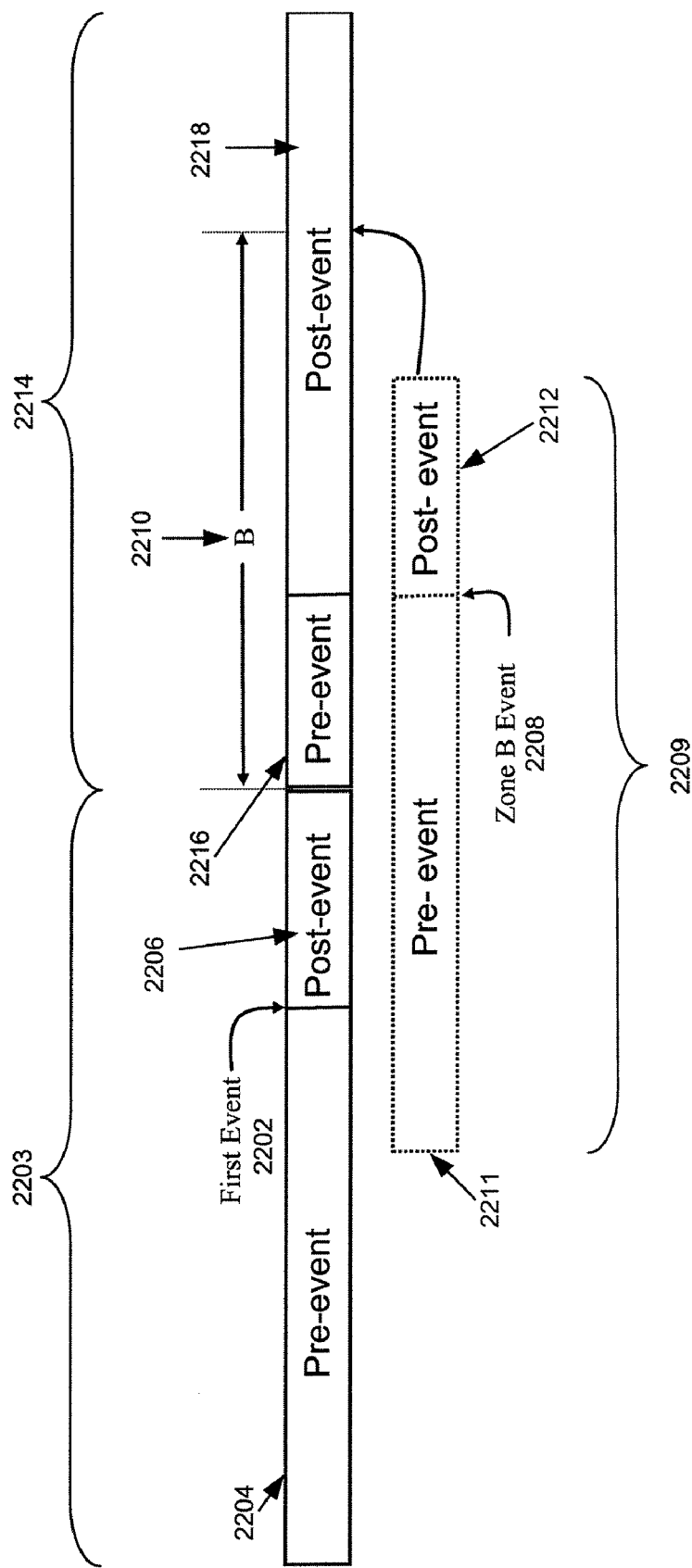
FIG. 8 shows a second scenario of an overlap of events recording in accordance with an aspect of the invention.
Figure 9:
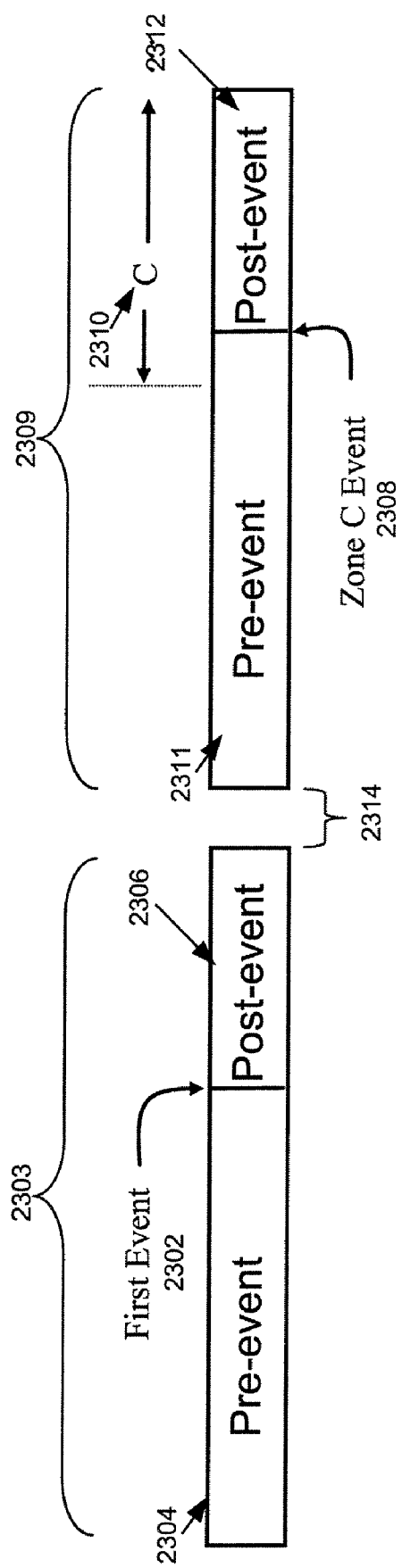
FIG. 9 shows a third scenario with no overlap of events recording in accordance with an aspect of the invention.

FIGS. 7-9 illustrate various data overlapping scenarios in accordance with various aspects of the invention. The various data overlapping and non-overlapping scenarios have been named zone A, zone B, and zone C for illustrative purposes. Zone events refer to specific events which may be triggered automatically by various algorithms or other inputs for example telemetry commands from a patient device. Other inputs may include a manual trigger issued by a patient or healthcare provider. In an embodiment of the invention, various types of triggers may cause the implantable medical device to store waveform data. The triggers may include an implantable seizure detection algorithm which monitors EEG channels for seizure activity. In addition, the triggers may include cardiac arrhythmia detection logic to monitor ECG signals. Moreover, the triggers may include manual triggers operated by a patient through a patient programmer.

In accordance with an aspect of the invention, an implantable medical device stores loop recording of waveform data having specified pre-event and post-event times. The implantable medical device includes a multitude of sense channels to process numerous signal types.

Overlaps as used in the below examples occur when the storing of data related to a second event overlaps the storing of data from a first event. Because data relating to both events may be stored non-redundantly, memory capacity for additional events is diminished.

In FIG. 7, a first event 2102 is illustrated along with its associated first event recording 2103. The first event recording 2103 includes a pre-event time 2104 and a post-event time 2106. In addition, a second event or zone A event 2108 is also illustrated in FIG. 7 along with its associated second event recording 2109. A zone A overlap occurs after the first event 2102 and while the implantable device is still writing the post-event section 2106 of the first event recording 2103. The zone A overlap time period is labeled as "A" (2110) in FIG. 7. The zone A event 2108 includes a pre-event time 2111 and post-event time 2112. The zone A event recording 2109 is illustrated as a dotted box to show the recording that would have been made had event 2108 occurred without the occurrence of event 2102.

In accordance with an aspect of the invention, a separate second loop recording 2109 does not need be recorded as recording 2103 is already storing waveform data that contains event 2108. A second loop recording 2109 is not captured as it would duplicate data already stored in memory. Though event 2108 does not generate a separate loop recording an entry would be generated in an event log to log the occurrence of the zone A event 2108.

FIG. 8 illustrates a second overlapping scenario in accordance with an aspect of the invention. In FIG. 8, a first event 2202 is shown along with its associated first event recording 2203. The first event recording 2203 includes a pre-event time 2204 and a post-event time 2206. In addition, a zone B event 2208 is also illustrated in FIG. 8 along with its associated zone B event recording 2209. A zone B overlap may occur when the zone B event 2208 occurs later than the end of the post-event section 2206 of the first event recording 2203, but early enough that there would be overlap between the first event recording 2203 and the zone B recording 2209. The zone B overlap time is labeled as "B" (2210) in FIG. 8. The zone B event 2208 includes a pre-event time 2211 and post-event time 2212. The zone B event recording 2209 is illustrated as a dotted box to show that this loop does not get recorded. Event recording 2209 shows the timing of the loop that would have been recorded had the event occurred independently of event 2202.

In accordance with an aspect of the invention, a second recording 2214 begins to write immediately after completion of the first event recording 2203 as illustrated by recording 2214. The second recording 2214 includes a second pre-event time 2216 and a second post-event time 2218. The second event recording 2214 includes the same information as the zone B event recording 2209 except that the pre-event time intervals and post-event time intervals have been modified. However, the total recording time for each of the second event recording 2214 and zone B recording 2209 remains the same. The second event recording 2214 results in two contiguous blocks of data, 2203 and 2214, stored in memory of the implantable device. However, the two recordings may be considered separate for the purposes of a priority algorithm. For example, if the first event was an ISDA trigger and the second event was the end of a seizure cluster, the ISDA trigger may be considered more important than the end of cluster event. In this case, the second loop recording may get overwritten before the first loop recording if the memory was filled and space was needed for a new loop recording.

FIG. 9 shows a third scenario in which overlapping does not occur. In FIG. 9, a first event 2302 is shown along with its associated first event recording 2303. The first event recording 2303 includes a pre-event time 2304 and a post-event time 2306. In addition, a zone C event 2308 is also illustrated in FIG. 9 along with its associated zone C event recording 2309. The zone C recording 2309 includes a pre-event time 2311 and post-event time 2312. A zone C event 2308 occurs when the event is late enough that there would be no overlap between two event loops. This time period is labeled as "C" (2310) in FIG. 9. In this case, the zone C recording 2309 may be written to memory. A time gap 2314 may exist between the first event recording 2303 and a zone C recording 2309.

Figure 10:
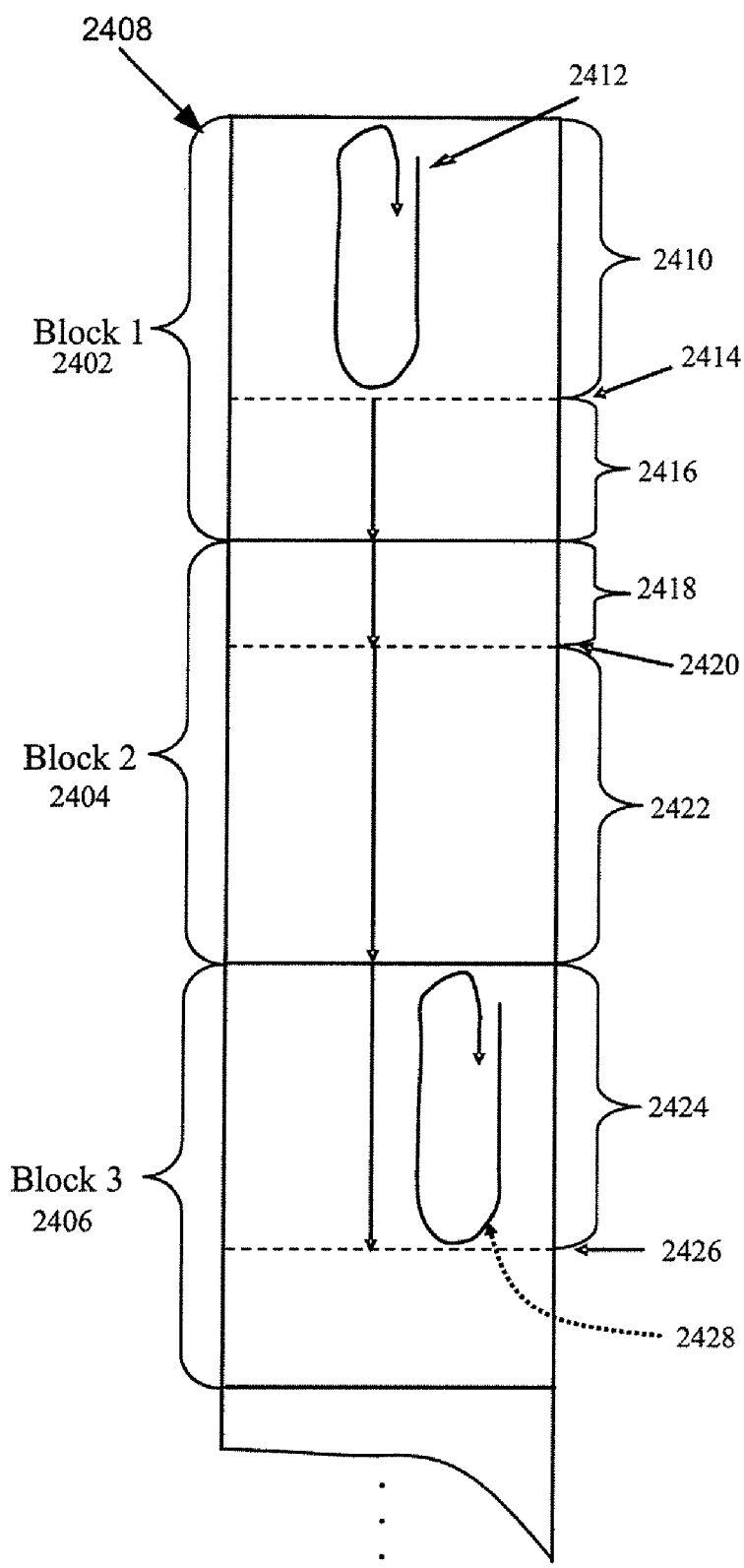
FIG. 10 shows an example of storing event data from multiple events in accordance with an aspect of the invention.
Figure 11:
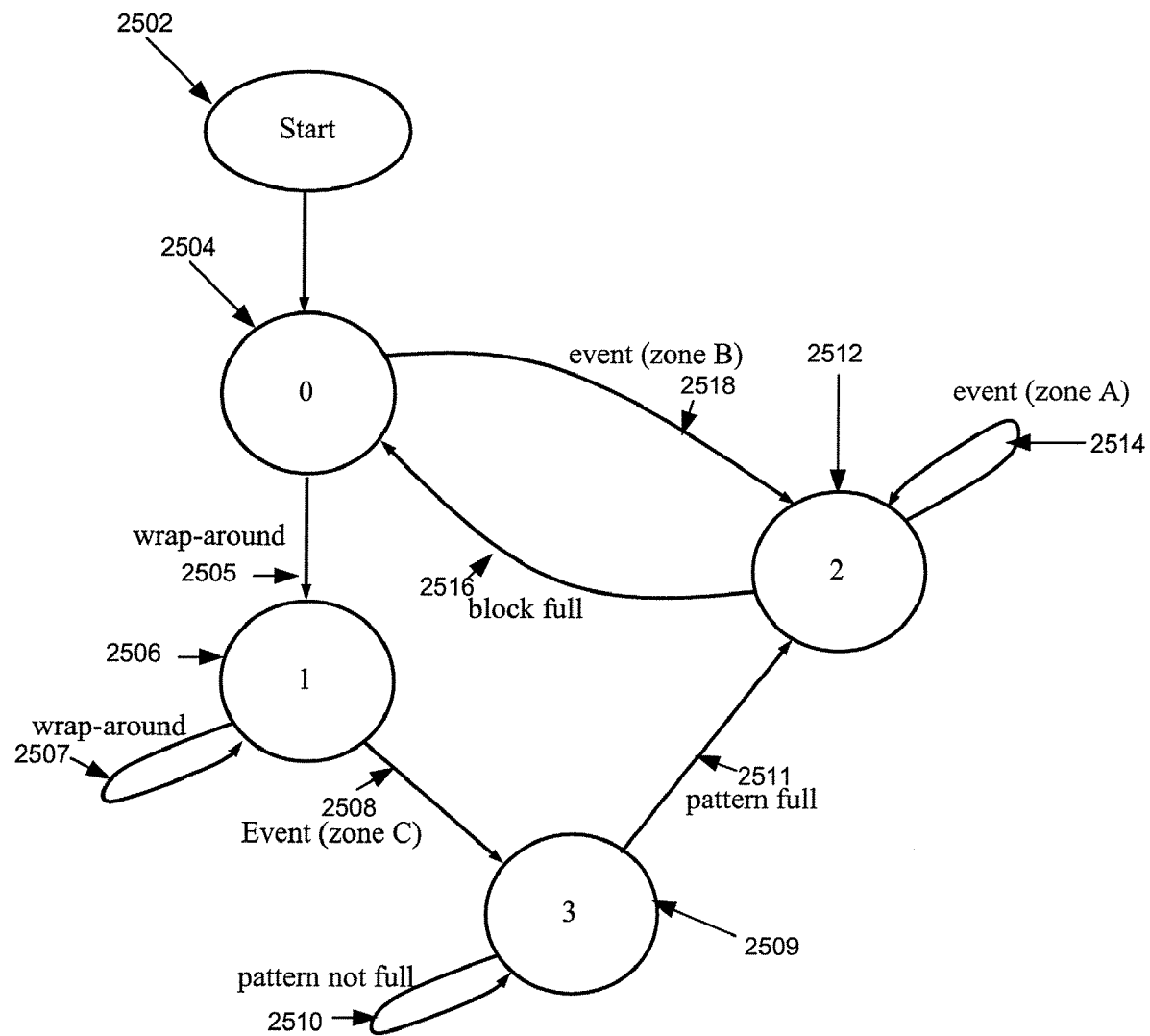
FIG. 11 shows a state transition diagram for loop recording in accordance with an aspect of the invention.

FIG. 10 illustrates an example of storing event data for multiple events, the events being triggered by different event triggers. FIG. 11 illustrates a state transition diagram which will be discussed in relation to the illustrative example of FIG. 10. In FIG. 10, three blocks of memory 2402, 2404, and 2406 are displayed for memory 2408. Those skilled in the art will realize that only a portion of memory 2408 is displayed in FIG. 10 as memory 2408 may contain numerous blocks for data storage. In addition, memory blocks 2402, 2404, and 2406 are shown as consecutive memory locations for illustrative purposes but as those skilled in the art will realize these displayed consecutive memory locations are not meant to be limiting as non-consecutive memory locations may also be used in accordance with various aspects of the invention.

In an aspect of the invention, a loop recording begins in memory block 2402. As illustrated in the state transition diagram of FIG. 11, a transition is made from the "start" position 2502 to state "0" 2504. State "0" 2504 may be entered whenever a new memory block starts to be written, such as upon startup 2502. As shown in FIG. 10, at position 2410 loop recording may occur. In addition, wrap-around may occur as illustrated at 2412. As further illustrated in FIG. 11, when a wrap-around 2505 occurs a transition is made from a state "0" 2504 to a state "1" 2506. Any number of wrap-arounds may occur while the recording is in this state. Numerous wrap-arounds 2507 may occur as illustrated in FIG. 11 in state "1" 2506.

At position 2414 of FIG. 10 an event occurs. In an aspect of the invention, a pointer may be stored to unroll the loop recording in the right order. The event may be an event such as an ISDA (implantable seizure detection algorithm) trigger which monitors EEG channels for seizure activity. In the transition state diagram of FIG. 11, when the transition occurs in state "1" 2506, it may be a zone "C" event 2508 and a transition is made from state "1" 2506 to state "3" 2509. State "3" 2509 may ensure that a full pattern has been written to a pre-event portion of an event recording before moving to a post-event recording. In addition, state "3" may be present to deal with differences in per channel data rate, which can vary due to differences in data compression settings, for example. If a full pattern has not been written to a pre-event portion of an event recording then a transition may not be made from state "3" 2509 as it may loop around in loop 2510.

When the pre-event section of an event recording has been filled as shown in 2511 a transition from state "3" 2509 to a state "2" 2512 may be completed. State "2" 2512 may occur when a loop recording has been committed to be made. Any events that occur while the system is in state "2" 2512 may be zone A events 2514. Referring back to FIG. 10 at position 2416, the post-event portion is being recorded in memory block 2402. During this time any number of additional zone A events may occur. The zone A events 2514 get logged but may not trigger any further storage of data beyond the memory block that has already been committed. All data written into memory during this state may go into the post-event portion of the event recording. When the block is full 2516, the system may transition from state "2" 2512 to state "0" 2504 and begin to write into a new memory block. In particular as shown in FIG. 10, the post-event recording may continue into a memory block 2404 as illustrated in FIG. 10 at position 2418.

When in state "0" 2504 the system may be looking for a zone B event 2518. At position 2420 of FIG. 10, a zone B event occurs. In this particular example, memory block 2404 is contiguous with memory block 2402. The zone B event may be marked and in FIG. 11 a transition from state "0" 2504 to state "2" 2512 may be completed. As wrap-around did not occur just prior to the zone B event the pre-event recording of the zone B event will be shorter than the pre-event recording of the earlier recorded event.

In FIG. 10, as position 2422, the post-event portion of the event recording is recorded in memory block 2404. While in state "2" 2512 any number of zone A events may occur.

Next, at position 2424 the loop recording may be continued into memory block 2406. As data is being written into a new memory block, memory block 2406, a transition from state "2" 2512 to state "0" 2504 may be accomplished. While in state "0", the system may search for additional zone B events.

At position 2426, a pointer may reach a pre/post boundary with no additional zone B events. As no additional zone B events have occurred, at position 2428 the system may continue to loop record. As the system may be in wrap-around, a transition from state "0" 2504 to state "1" 2506 may be completed. Next, the system may search or wait for a zone C event. Memory block 2406 may or may not be contiguous with memory block 2404. If no event occurs before uplink, memory block 2406 may not be uplinked for analysis.

According to an additional aspect of the invention, it may be possible to transition from a state "1" 2506 to a state "2" 2512 through state "3" 2509 during one sample period. Moreover, in accordance with various embodiments of the invention, a zone B event may not require a trip to state "3" 2509, because the loop recording may not need to be unrolled. The block size may ensure that an integer number of full patterns will be in the block.

Figure 12:
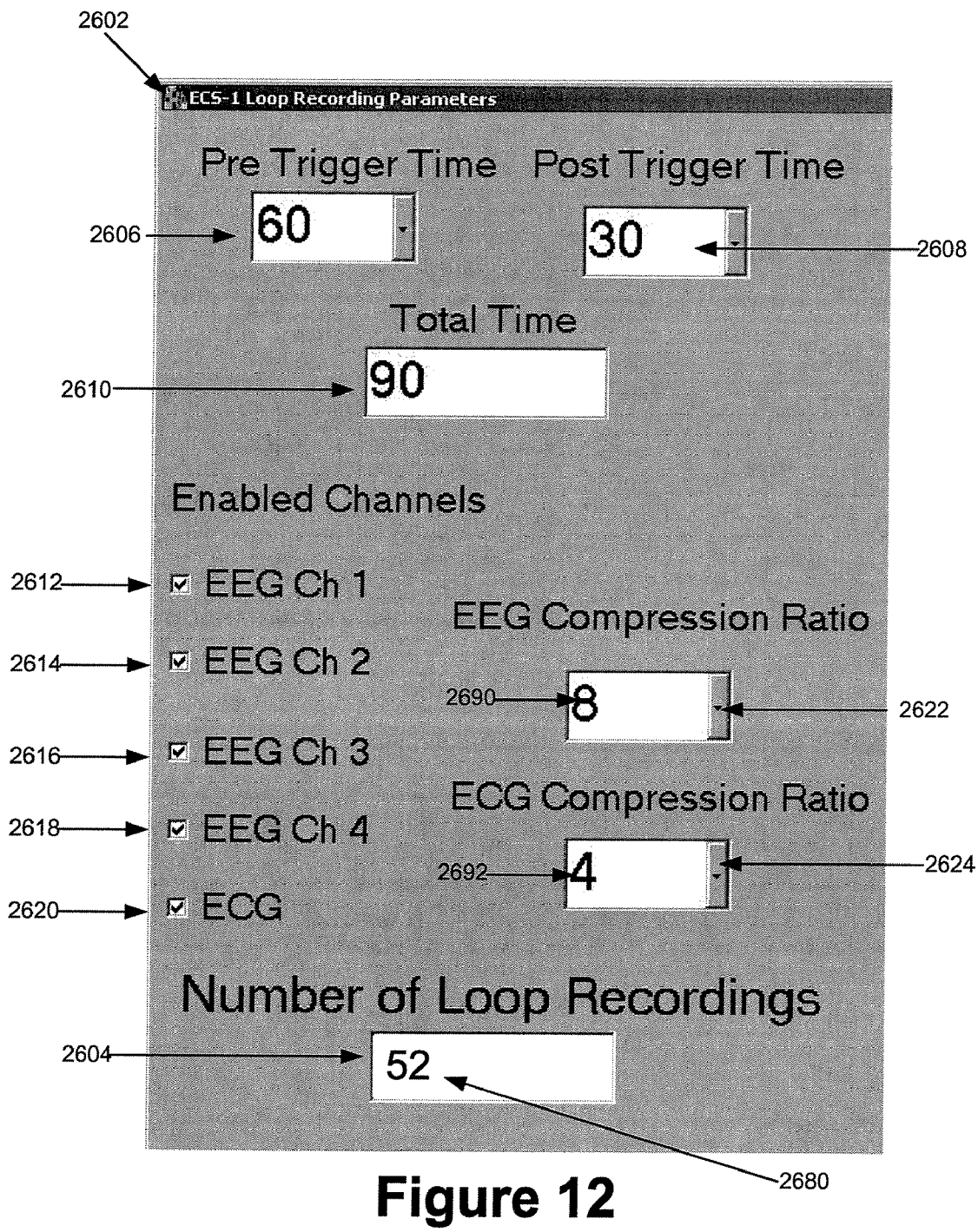
FIG. 12 shows a graphical user interface that may be used in accordance with an aspect of the invention.

FIG. 12 shows a graphical user interface 2602 that may be used in accordance with various aspects of the invention. In one aspect of the invention, a device having a fixed amount of memory may use this graphical interface to determine the number of loop recording 2604 that may be stored in the device. For example, an implantable device may have a total of 2 MB of memory to store log and loop recording data. A certain portion of the memory may be needed to store or log events in an event log or for other non-loop recording storage purposes. This space may be on the order of 200 K of memory. The remaining 1.8 MB of memory may be allocated for storing waveform data associated with the events. As those skilled in the art will realize, a device such as an implantable device may have more or less memory for use in storing waveform and other data. Furthermore, the allocation of memory may be configurable. The above example in only one illustrative example and is not intended to limit the described aspects of the invention.

In FIG. 12, based on the available amount of memory, selected criteria, and details of recording and storage, the number of loop recording 2604 that may be stored is displayed. The selected criteria may include a pre-trigger time 2606, a post-trigger time 2608, and a total time 2610. For example, the selected pre-trigger time 2606 may be 60 seconds, whereas, the selected post-trigger time 2608 may be 30 seconds. The total time 2610 may be the result of the pre-trigger time 2606 and the post-trigger time 2608, ninety seconds. Those skilled in the art will realize that the amount of time selected for the pre-trigger time 2606 and post-trigger time 2608 may depend on the frequency of events and other factors considered by a user. For example, a physician or other caregiver may set the pre-trigger time 2606 and post-trigger time 2608 based on the type of event which they expect to record in order to produce useful data for analysis.

Figure 13:
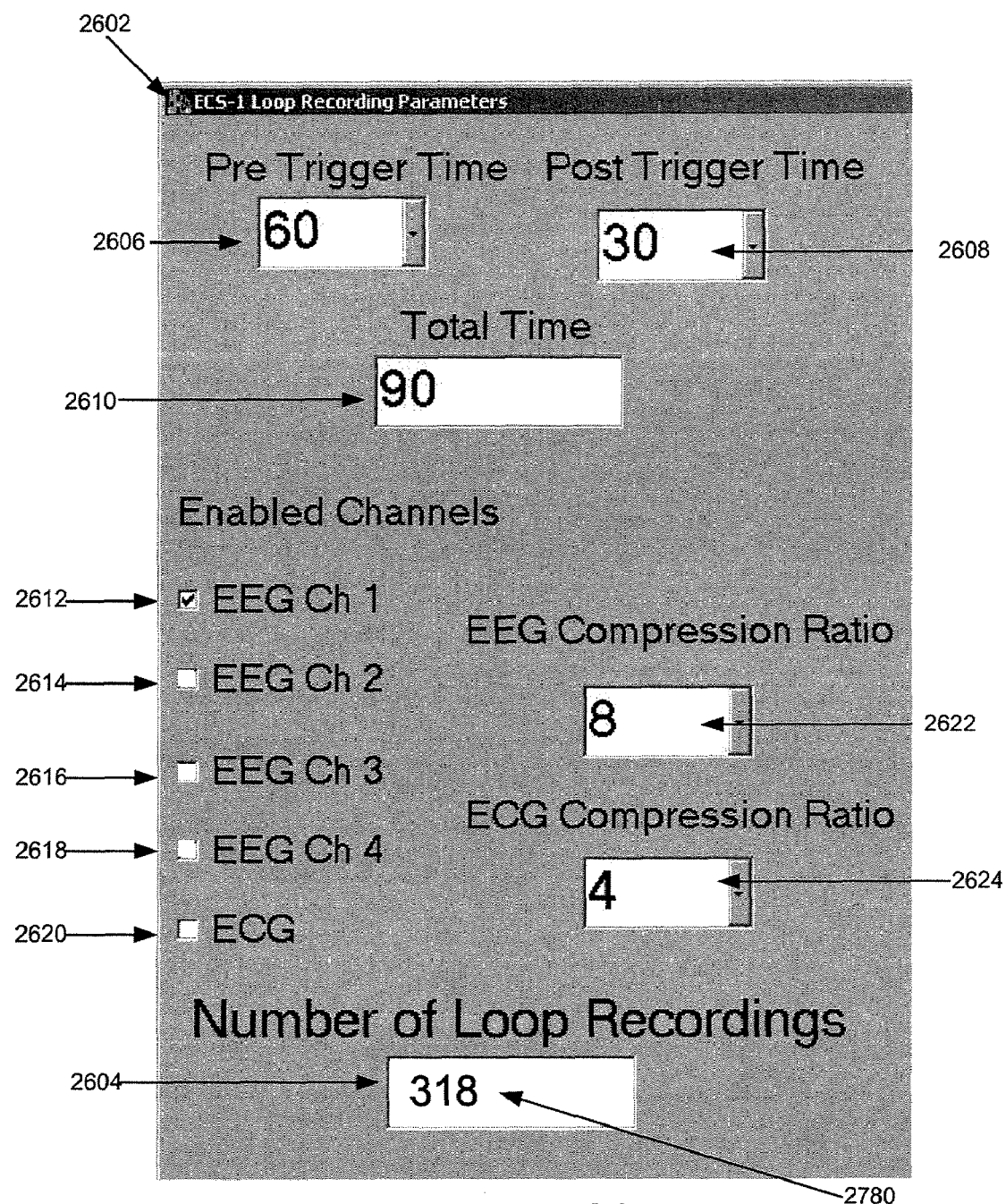
FIG. 13 shows an alternative graphical user interface that may be used in accordance with an aspect of the invention.

In FIG. 12, various channels may be enabled to collect event information. For instance, a physician or caregiver may select to record information from EEG channel "1" 2612, EEG channel "2" 2614, EEG channel "3" 2616, and EEG channel "4" 2618. In addition, data relating to an ECG channel 2620 may also be recorded. The number and type of channels selected may affect the maximum number of loop recording 2604 that may be saved. In particular, increasing the number of enabled channels to be recorded decreases the maximum number of loop recordings that that may be saved in the device. For example, FIG. 12 illustrates that with EEG channels 1-4 (2612-2618) and ECG channel 2620 enabled and with a pre-trigger time 2606 of 60 seconds and a post-trigger time 2608 of 30 seconds, the number of loop recording 2604 that may be saved is "52" (2680). In contrast, as shown in FIG. 13 if only one channel is selected such as EEG channel "1" 2612 and the pre-trigger time 2606 of 60 seconds and the post-trigger time 2608 of 30 seconds remains the same, the number of loop recording 2604 that may be saved increases to "318" (2780). As those skilled in the art will realize, by manipulating the pre-trigger time 2606, post-trigger time 2608, the enabled channels (2612-2620), and recording details like compression, a physician or caregiver may obtain a particular number of loop recording 2604 to analyze.

Moreover, data compression may be used to store an additional number of loop recording or a longer record time for the same number of loop recording. FIG. 12 illustrates fixed ratio data compression for multiple types of physiologic signal channels (both EEG and ECG). For example, an EEG compression ratio 2622 may be selected by a physician or caregiver. Because an objective of loop recording may be to provide to physician or caregiver with waveforms for visual analysis, the data compression may be lossy, as long as it does not distort the signal to the point where the physician or caregiver is unable to make an accurate diagnosis.

In an aspect of the invention, four EEG channels are available (2612-2618) and enabled for recording (FIG. 12). In an embodiment, all enabled EEG channels (2612-2618) may have the same compression settings. For EEG (or other signal) compression, the ratios 2622 may include the following compression ratios as shown in Table 1. Table 1 also includes a brief description of the compression technique that may be implemented to achieve the selected compression ratio.

TABLE 1

| EEG Compression | |
|---|---|
| 1:1 | No compression |
| 2:1 | Delta companding |
| 4:1 | NTP, delta companding |
| 8:1 | NTP, NTP, delta companding |
| 16:1 | NTP, NTP, range companding, D/R |

The EEG compression ratios 2622 may be selectable through use of a dropdown box in graphical user interface 2602. In FIG. 12, the EEG compression ratio is "8" (2690).

In another aspect of the invention, ECG channel 2620 may also be available for compression. In an embodiment, ECG channel 2620 may be compressed using an ECG compression ratio 2624 as illustrated in Table 2. Table 2 also includes a brief description of the compression technique that may be implemented to achieve the selected compression ratio.

TABLE 2

| ECG Compression | |
|---|---|
| 1:1 | No compression |
| 2:1 | Delta companding |
| 4:1 | NTP, delta companding |

The ECG compression ratios 2624 may also be selectable through use of a dropdown box in graphical user interface 2602. In FIG. 12, the EEG compression ratio is "4" (2692). The number of loop recording based on the selected channels (EEG and ECG), compression ratios (EEG and ECG), and selected times (2606 and 2608) is "52" (2680).

As those skilled in the art will realize, other compression ratios for either the EEG, ECG, or other physiologic signal channels or any combination thereof may be utilized as the physician or clinician may desire to set compression parameters not listed in these tables. In the case of a non-default choice, an advanced compression settings widget (e.g. button or tab; not shown) may be available to the user allowing greater flexibility in the setting of compression ratios. As an alternative, all compression settings may be placed in an advanced dialog box to simplify the main loop recording user interface.

Figure 14:
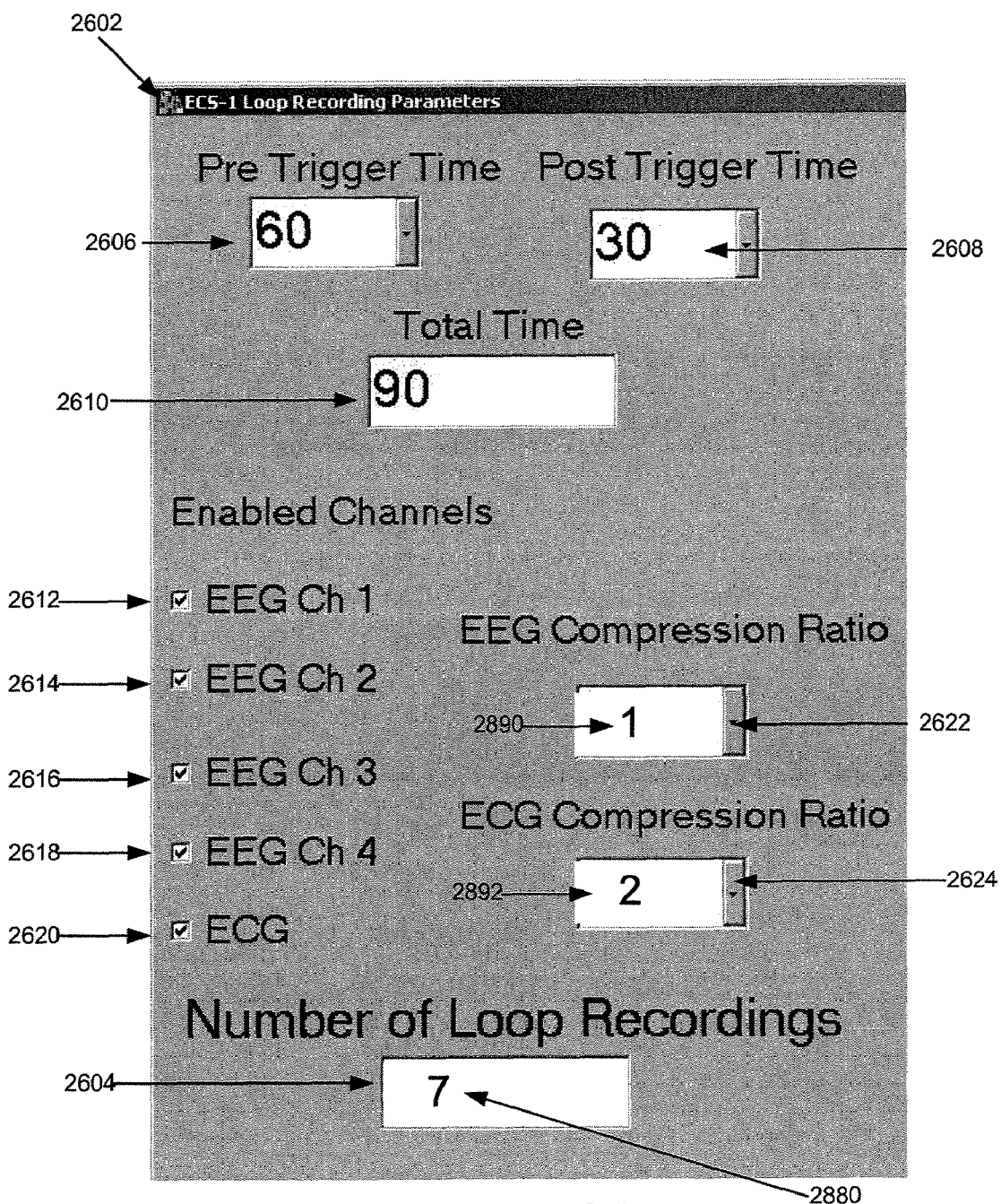
FIG. 14 shows another example of a graphical user interface that may be used in accordance with an aspect of the invention.

A change in the compression ratios for EEG channels (2612-2618) and ECG channel (2620) is illustrated in FIG. 14, in accordance with an aspect of the invention. In FIG. 14, the EEG compression ratio 2622 is "1" (2890) and the ECG compression ratio 2624 is "2" (2892). The number of associated loop recording 2604 based on the selected factors in user interface 2602 is "7" (2880). As illustrated, the number of loop recording has been reduced from "52" (2680) to "7" (2880).

Figure 15:
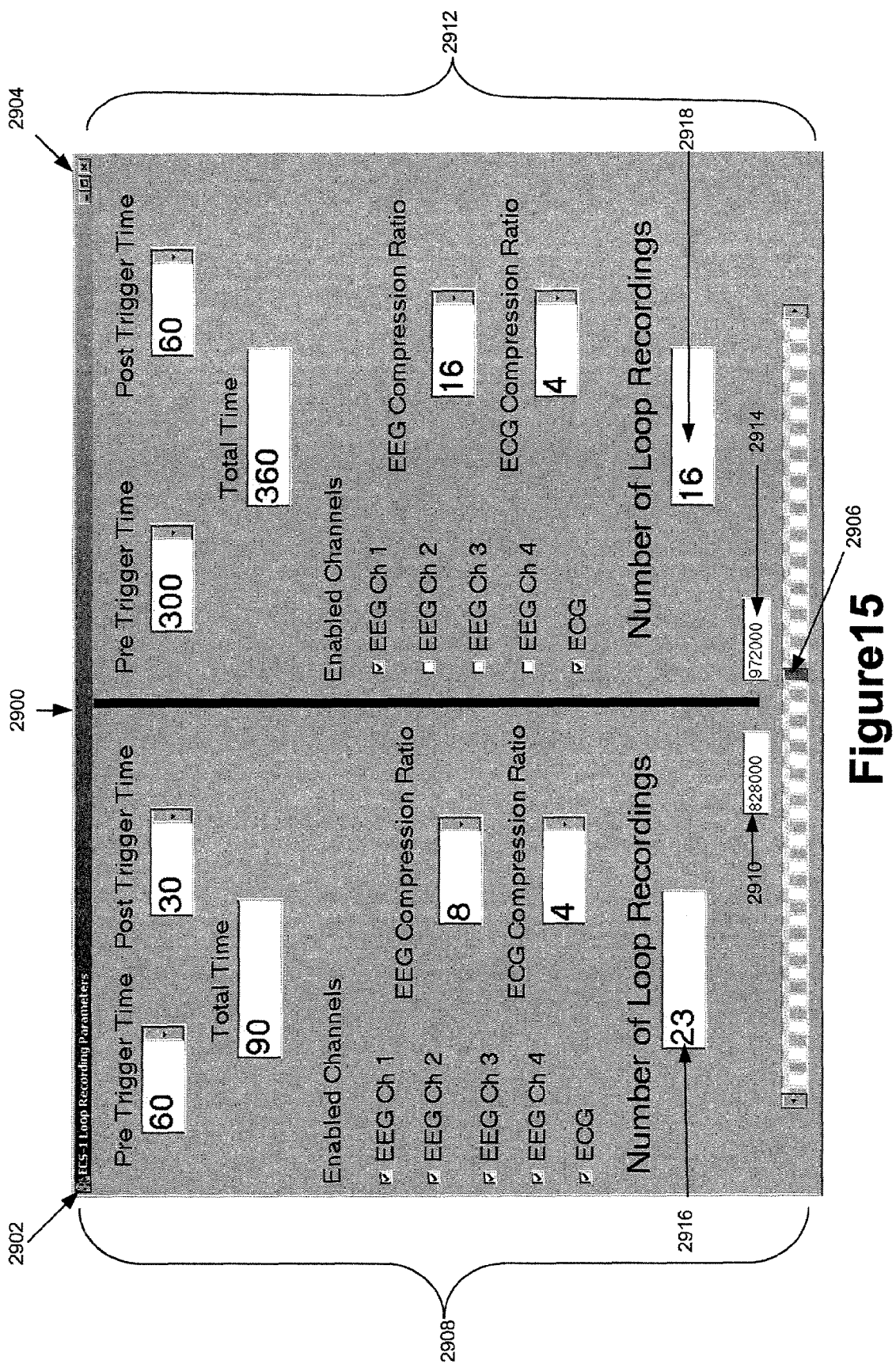
FIG. 15 shows a spilt memory mode and an associated split screen graphical user interface in accordance with an aspect of the invention.

FIG. 15 represents a spilt memory mode in accordance with an aspect of the invention. The split memory mode may include two separate instances of a loop recording algorithm, each operating independently. The split screen graphical user interface of FIG. 15 may allow both separate instances of a loop recording algorithm to be configured independently. In FIG. 15, a spilt screen graphical user interface 2900 comprising a left half screen 2902 and a right half screen 2904. Both screens contain similar selection criteria for determining a number of loop recordings to be recorded. Spilt screen graphical user interface 2900 may be used to allow two different configurations for loop recording. The different configurations may each be apportioned an amount of memory to be used for loop recordings. For example, a slider 2906 may be used to split the available waveform memory between the two different configurations.

In an example, a total amount of memory useable for waveform loop recording may be 1,800,000 bytes. The 1,800,000 bytes of memory for waveform loop recording may be based on a 2 MB memory capacity, less storage for other non-waveform data. As shown in FIG. 15, the slider 2906 may adjust the amount of memory apportioned to each of the different configurations. In one aspect of the invention, a first configuration 2908 may have available 828,000 bytes (2910) of memory whereas a second configuration (2912) may have 972,000 bytes (2914) of memory available for loop recordings. The 828,000 bytes (2910) of memory may allow "23" (2916) loop recordings based on the selected criteria as illustrated in left hand screen 2902. Furthermore, 972,000 bytes (2914) of memory may allow "16" (2918) loop recordings based on the selected criteria. By using slider 2906, the amount of memory available to each configuration may be altered with the corresponding number of loop recording available displayed to the physician or caregiver.

Thus, various embodiments of the invention have been disclosed. One skilled in the art will appreciate that the above teachings may be practiced with embodiments other than those disclosed. The disclosed embodiments are presented for purposes of illustration and not limitation, and the inventions are limited only by the claims that follow.

What is claimed:

1. A method of handling multiple loop recording in an implantable device, the method comprising:
   (a) monitoring a first signal set including first waveform data, the first waveform data associated with a physiologic condition;
   (b) detecting a first event;
   (c) initiating a first loop recording, the first loop recording activated by the first event, the first loop recording storing at least a portion of the waveform data of the first signal set, the first loop recording including a pre-event time and a post-event time;
   (d) monitoring a second signal set including second waveform data;
   (e) detecting a second event;
   (f) determining if an overlap of data will occur between the first loop recording and a second loop recording associated with the second event; and
   (g) if based on the determination in (f) that an overlap of data will occur, determining whether to initiate the second loop recording, the determination further comprising:
      (i) determining if the second event occurs while recording the post-event time of the first loop recording: and if in (i) the second event occurs while recording the post-event time of the first loon recording, then
      (ii) completing the first loop recording and not initiating the second loop recording.

2. The method of claim 1, wherein the first signal set and the second signal set are the same.

3. The method of claim 1, wherein the first event comprises a first trigger, the first trigger including an electrocardiogram trigger.

4. The method of claim 1, wherein the first event comprises a first trigger, the first trigger including a seizure detection algorithm trigger.

5. The method of claim 1, wherein the first event comprises a first trigger, the first trigger including a manual trigger.

6. The method of claim 1, wherein the second event comprises a second trigger, the second trigger including an electrocardiogram trigger.

7. The method of claim 1, wherein the second event comprises a second trigger, the second trigger including a seizure detection algorithm trigger.

8. The method of claim 1, wherein the second event comprises a second trigger, the second trigger including a manual trigger.

9. A method of handling multiple loop recording in an implantable device, the method comprising:
   (a) monitoring a first signal set including first waveform data, the first waveform data associated with a physiologic condition;
   (b) detecting a first event;
   (c) initiating a first loop recording, the first loop recording activated by the first event, the first loop recording storing at least a portion of the waveform data of the first signal set, the first loop recording including a pre-event time and a post-event time;
   (d) monitoring a second signal set including second waveform data;
   (e) detecting a second event;
   (f) determining if an overlap of data will occur between the first loop recording and a second loop recording associated with the second event; and
   (g) based on the determination in (f), determining whether to initiate the second loop recording, the determination to initiate the second loop recording comprising:
      (i) determining if the second event occurs after recording of the post-event time of the first loop recording; and if in (i) the second event occurs after recording of the post-event time of the first loop recording, then
      (ii) initiating the second loop recording after completion of the first loop recording.

10. The method of claim 9, wherein the first loop recording and the second loop recording are contiguous.

11. The method of claim 9, wherein the first loop recording and the second loop recording comprise substantially similar recording times.

12. An implantable medical device comprising:
   (a) a first monitoring element that receives a first signal set associated with a physiologic condition;
   (b) a second monitoring element that receives a second signal set;
   (c) a storage medium; and
   (d) a processing module coupled to the storage medium and programmed with computer-executable instructions for performing:
      (i) detecting a first event;
      (ii) initiating a first loop recording, the first loop recording activated by the first event, the first loop recording storing waveform data of the first signal set in the storage medium, the first loop recording including a pre-event time and a post-event time;
      (iii) detecting a second event;
      (iv) determining if an overlap of waveform data will occur between the first loop recording and a second loop recording associated with the second event; and
      (v) if based on the determination in (iv) that an overlap of data will occur, determining whether to initiate the second loop recording, the determination further comprising:
         (I) determining if the second event occurs while recording the post-event time of the first loop recording; and if in (I) the second event occurs while recording the post-event time of the first loop recording, then
         (II) completing the first loop recording and not initiating the second loon recording.

13. An implantable medical device comprising:
   (a) a first monitoring element that receives a first signal set associated with a physiologic condition;
   (b) a second monitoring element that receives a second signal set;
   (c) a storage medium; and
   (d) a processing module coupled to the storage medium and programmed with computer-executable instructions for performing:
      (i) detecting a first event;
      (ii) initiating a first loop recording, the first loop recording activated by the first event, the first loop recording storing waveform data of the first signal set in the storage medium, the first loop recording including a pre-event time and a post-event time;

(iii) detecting a second event;

(iv) determining if an overlap of waveform data will occur between the first loop recording and a second loop recording associated with the second event; and (v) based on the determination in (iv), determining whether to initiate the second loop recording, the determination to initiate the second loop recording further comprising:

(I) determining if the second event occurs after recording of the post-event time of the first loop recording; and if in (I) the second event occurs after recording of the post-event time of the first loop recording, then (II) initiating the second loop recording after completion of the first loop recording.

* * * * *

UNITED STATES PATENT AND TRADEMARK OFFICE
CERTIFICATE OF CORRECTION

PATENT NO. : 7,610,083 B2 Page 1 of 1
APPLICATION NO. : 11/380575
DATED : October 27, 2009
INVENTOR(S) : Drew et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 533 days.

Signed and Sealed this

Twelfth Day of October, 2010

David J. Kappos
*Director of the United States Patent and Trademark Office*